United States Patent [19]

Orth

[11] Patent Number: 5,062,775
[45] Date of Patent: Nov. 5, 1991

[54] ROLLER PUMP IN AN EXTRA CORPOREAL SUPPORT SYSTEM

[75] Inventor: Jeffrey L. Orth, Salt Lake City, Utah

[73] Assignee: Rocky Mountain Research, Inc., Salt Lake City, Utah

[21] Appl. No.: 414,780

[22] Filed: Sep. 29, 1989

[51] Int. Cl.⁵ .............................................. F04B 43/12
[52] U.S. Cl. ...................................... 417/477; 417/319
[58] Field of Search ............................... 417/474–478, 417/319

[56] References Cited

U.S. PATENT DOCUMENTS

| | | | |
|---|---|---|---|
| 3,137,240 | 6/1964 | Hunt | 417/477 |
| 3,138,104 | 6/1964 | Cantor | 417/477 X |
| 3,698,381 | 10/1972 | Federico et al. | |
| 3,955,902 | 5/1976 | Kyvsgaard | |
| 3,963,023 | 6/1976 | Hankinson | 417/477 X |
| 4,043,712 | 8/1977 | Azzolini | |
| 4,174,193 | 11/1979 | Sakakibara | 417/477 |
| 4,218,197 | 8/1980 | Meyer et al. | |
| 4,412,793 | 11/1983 | Stenberg et al. | 417/477 |
| 4,522,571 | 6/1985 | Little | 417/476 |
| 4,530,647 | 7/1985 | Uno | |
| 4,548,553 | 10/1985 | Ferster | 417/477 |
| 4,552,516 | 11/1985 | Stanley | 417/477 |
| 4,558,996 | 12/1985 | Becker | 417/477 X |
| 4,573,884 | 3/1986 | Troutner | 417/477 X |
| 4,573,887 | 3/1986 | Smith | 417/477 |
| 4,662,355 | 5/1987 | Pieronne et al. | |
| 4,886,431 | 12/1989 | Soderquist et al. | 417/477 |
| 4,909,713 | 3/1990 | Finsterwald et al. | 417/477 |

*Primary Examiner*—Leonard E. Smith
*Assistant Examiner*—Eugene L. Szczecina, Jr.
*Attorney, Agent, or Firm*—Trask, Britt & Rossa

[57] ABSTRACT

An extracorporeal support system has an inlet catheter which is positioned with its distal end in the right atrium or vena cava of the patient. A roller pump with an inlet pressure sensor is positioned close to its inlet to sense the pressure in the inlet line which pumps the blood through the system to any output catheter positioned in the arterial system of the patient. The system has a shunt with blocking valves to block the flow automatically in the event of an unsafe condition. The system has a microprocessor-based controller for automatic operation of the system components including a servomotor for driving the roller pump at a speed to precisely maintain the inlet pressure at a preselected point. The system includes a blood treatment device such as an oxygenator. The roller pump has an axially adjustable head which is also removable.

12 Claims, 24 Drawing Sheets

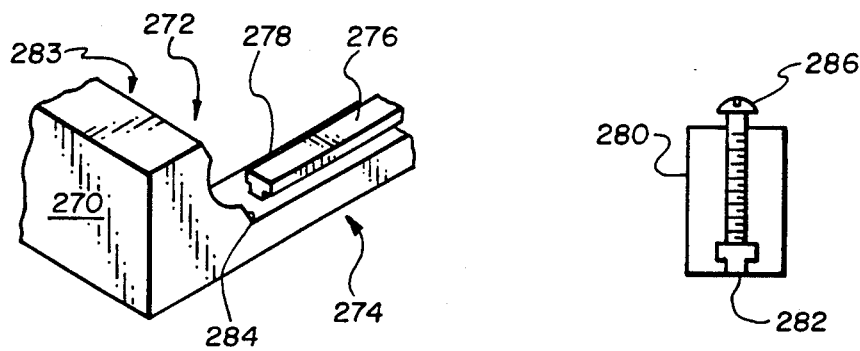
Fig. 6
Fig. 7
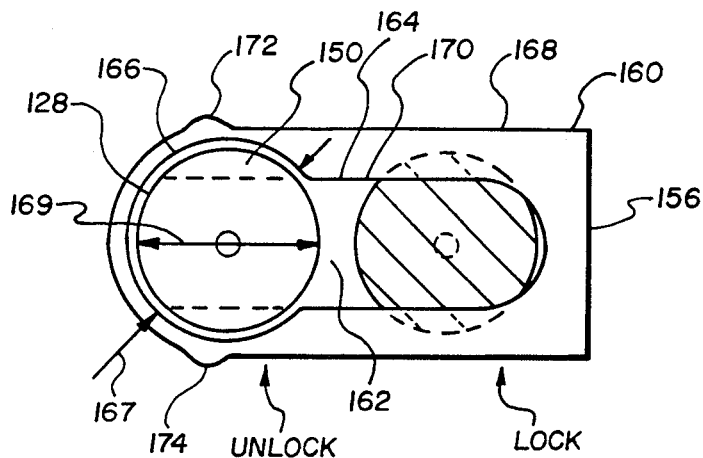
Fig. 8
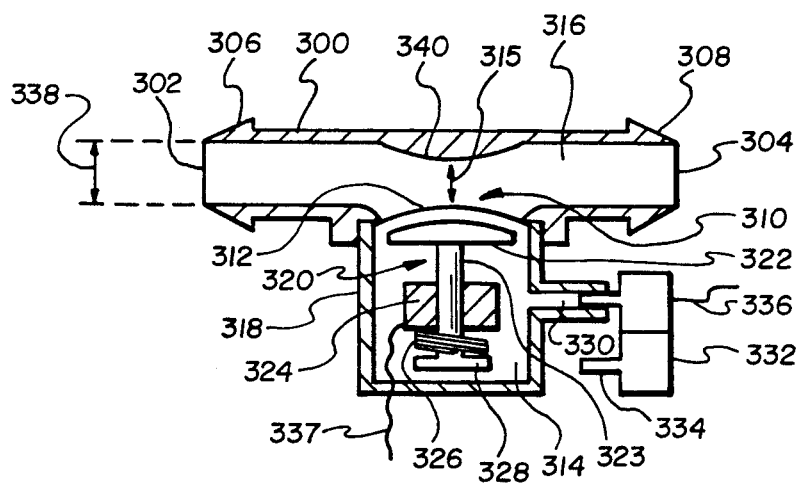
Fig. 9

ROLLER PUMP IN AN EXTRA CORPOREAL SUPPORT SYSTEM

BACKGROUND OF THE INVENTION

1. Field

This invention relates to support systems suitable for treating the blood of a patient outside of the body and returning the blood to the body as part of a medical treatment or life support activity. This invention also includes a roller pump for use in the support system.

2. State of the Art

Today a variety of medical treatments involve procedures by which the blood of a patient is processed through an external or extracorporeal system. For example, the blood may be removed for dialysis or for oxygenation.

In the same vein, various surgical procedures involving the heart may require diversion of the blood from the cardiopulmonary system until completion of the involved surgical procedures.

Systems for extracorporeal support of a patient are known. For example U.S. Pat. No. 4,662,355 (Pieronne) discloses a pump regulation system which may be used for regulation of the bypass circuit of an artificial kidney and a cardiopulmonary system. Various components for use in such systems are available commercially. For example, Seabrook Medical Systems, Inc. of Cincinnati, Ohio offers a blood warming unit for warming the blood before it is returned to the patient and a bladder holder for use as an inlet reservoir for a pump. Seabrook Medical Systems, Inc. also offers a pump controller as well as a cart for mounting or positioning selected components of an extracorporeal support system.

Canyon Medical Products of Salt Lake City, Utah offers percutaneous femoral bypass cannulation systems which may be suitable for interconnecting extracorporeal support systems to a patient. Stockert-Shiley of Irvine, Calif. offers pressure control modules for use in extracorporeal support systems. C. R. Bard, Inc. of Billerica, Mass. even offers a complete extracorporeal cardiopulmonary support system as a commercial product.

Commercial components and systems available today have typically been available for adult patients and some infants. Newborns may need temporary cardiopulmonary support when suffering respiratory failure or a fulminant disease leading to respiratory failure. Extracorporeal support for newborns (neo-nates) has been successfully employed for over 10 years. The procedure has been described in several professional journals. R. H. Bartlett, et al., EXTRA CORPOREAL MEMBRANE OXYGENATION (ECMO) CARDIOPULMONARY SUPPORT IN INFANCY, Trans. Amer. Soc. Artif. Int. Organs, 1976, p. 80-93 (Vol. XXII); R. H. Bartlett, et al., EXTRA CORPOREAL CIRCULATION (ECMO) IN NEO-NATAL RESPIRATORY FAILURE, Jnl. of Thor. and Card. Surgery, 1977, p. 826-33 (Vol. 74, No. 6); L. Gattinoni, et al., REVERSAL OF TERMINAL ACUTE RESPIRATORY FAILURE BY LOW FREQUENCY POSITIVE PRESSURE VENTILATION WITH EXTRA CORPOREAL REMOVAL OF $CO_2$ (LFPPV-$ECCO_2R$), Trans. Am. Soc. Artif. Internal Organs, 1981, p. 289-93, (Vol. XXVII); and W. Fukui, et al., A PORTABLE, PUMPLESS, AV BY-PASS $ECCO_2R$ SYSTEM WITH A HOLLOW FIBER MEMBRANE LUNG, 1986, Tran. Soc. Artif. Internal Organs, p. 521-24 (Vol. XXXII).

Extracorporeal support for neonates is monitored by a national central registry. It now has recorded data for over 1800 patients receiving such treatment. Notably, newborns have rather small blood volume (e.g. 1 liter or less) and are therefore quite difficult to treat because an external support system requires a volume of blood to work. Further, any extracorporeal support system inherently involves the use of substantial amounts of heparin in order to minimize clotting, not only in the system but also internally within the patient. As a result, it is presently understood that extracorporeal support of neonates has been limited to those weighing approximately more than 2 kilograms and who are typically more than 35 weeks gestation at birth. Nonetheless, there are a considerable number of neonates who are candidates for extracorporeal support, but who are not of sufficient size to successfully undergo treatment.

It is presently understood that many of the neonates who qualify for the treatment are inherently poor risks for transport. Nevertheless, many of the neonate patients reported to the national central registry were born away from the treating center and were necessarily transported. Under these circumstances, there is a compelling and growing need for an extracorporeal support system to deal with neonates presently untreatable and to improve the ability to transport all neonates. That is, there is a need for a more regulated, automated and more transportable extracorporeal support system. Notably, such a system would also be suitable for use not only with neonates but also with older patients, particularly those requiring transport. Further, a highly automated system may be desirable for use with all patients, regardless of age, because of the reduced involvement of attendant personnel in, for example, an intensive care unit (ICU). Additionally, a smaller and more compact system is desirable to reduce or minimize the risks of contamination from a larger system, and because of an increased need for heparin and the increased potential for hemolysis.

Efforts heretofore to miniaturize have been attempted. T. Kawamuri et al., EXTRA CORPOREAL MEMBRANE OXYGENATION (ECMO) IN PUMPLESS RIGHT VENTRICLE TO LEFT ATRIUM BY-PASS, 1985 Trans. Am. Soc. Artif. Intern. Organs, p. 616-620 (Vol. XXXI). The reported miniaturized system used the pressure gradient between the arterial and venous systems. However, in many circumstances, particularly in the context of an asphyxiated myocardium, such a pumpless system is believed to be inapplicable or unsuitable. Further, the devices described did not appear to be suitable for long-term use and became routinely nonfunctional after 24 to 48 hours when in typical neonate applications, the extracorporeal support may be required for periods up to 130 hours, if not more.

SUMMARY OF THE INVENTION

An extracorporeal support system has an inlet positioned to receive blood from the patient. Conduit means preferably of substantially constant diameter is provided to transport blood between the inlet and an outlet. The outlet is positioned to return the blood to the patient. Roller pump means is interconnected in the conduit means and configured to pump the blood through the conduit means. The roller pump means includes a motor to effect operation.

An inlet detecting means is interconnected in the conduit means between the inlet and the roller pump means to measure the pressure of the blood in the conduit means and to supply a signal reflective of the inlet blood pressure in the conduit means. Blood treatment means is interconnected in the conduit means downstream of the pump means to receive and treat the blood and also to supply the blood at its output. Control means is interconnected to the inlet detecting means to receive the signal reflective of the inlet blood pressure. It is also connected to the motor means to supply operation signals thereto. The control means supplies operation signals which vary the motor speed between a stop condition upon receipt of a signal reflective of a preselected "low" inlet blood pressure and a preselected high speed condition upon receipt of signal reflective of a preselected "high" inlet blood pressure.

In one embodiment, an upstream pressure detector is interconnected in the conduit means between the roller pump means and the blood treatment means; and a downstream pressure detector is interconnected in the conduit means between the outlet and the blood treatment means. The upstream and downstream pressure detectors each measure the pressures of blood in their respective locations and supply signals reflective of the blood pressure to the control means which in turn generates alarm signals when either one or both of the detected pressures differ from preselected pressures.

In another embodiment, an air detector is interconnected in the conduit means between the blood treatment means and the outlet means. The air detector detects the presence of air in the conduit means and generates a signal reflective thereof. The control means receives the signal reflective of air in the conduit means to generate an alarm signal. In a preferred arrangement, a shunt is interconnected in the conduit means at one end between the inlet and the inlet detecting means and at the other end between the blood treatment means and the outlet. A first solenoid valve means is interconnected between the shunt and the inlet, a second solenoid valve is interconnected in the shunt and the third solenoid valve is interconnected between the outlet and the shunt. Upon detection of air, the control means generates and sends operating signals to the first and third solenoid valves to block fluid flow in the conduit means and to the second solenoid valve to allow fluid flow through the shunt.

In an alternate embodiment, a second pump means is interconnected into the conduit means between the inlet means and the outlet means for metering fluids into the blood. Preferably it is interconnected between the roller pump means and the blood treatment means. The second pump means is desirably a syringe to insert fluids into the conduit means. Most preferably, the second pump means includes a motor device conductively connected to the control means to receive signals therefrom to operate the motor device and meter the fluid into the conduit.

The roller pump means of the extracorporeal support system preferably includes a housing with a top, bottom and front. The housing has a keyhole-shaped recess formed in the top extending inwardly therefrom. The recess has a throat with opposite sides opening through the front interconnecting with opposite ends of an arcuate recessed surface. Axle means is rotatably secured to the housing and extends into the recess substantially positioned with respect to the arcuate recessed surface.

Pump head means is removably secured to the axle means within the recess. The pump head means includes roller means positioned proximate the arcuate recessed surface for urging the conduit means against the arcuate recessed surface. The pump head means also includes locking means for removably securing the pump head to the axle.

Desirably, the locking means includes an engagement portion and a latch member positioned for operation by the user and operable between the first position in which the latch member engages the engagement portion to secure the pump to the axle means and a second position in which the latch member is disengaged from the engagement portion so that the pump head may be removed from the axle means.

In a preferred embodiment, adjustment means is interpositioned between the pump head means and the axle means for moving the pump head means axially toward and away from the axle means and in turn moving the roller means toward and away from the arcuate recessed surface.

Preferably, the adjustment means includes a follower positioned to move toward and away form the axle means and a screw means with a head accessible to the user. The screw means has threaded portions interconnecting the follower to the axle. The screw means is operable by the user to move the follower toward and away from the axle.

Desirably, the pump head means includes a sleeve for positioning over the follower. The engagement portion includes a key way formed partly in the sleeve and partly in the follower. The latch is desirably a key insertable into and removable from the key way. The arcuate recessed surface preferably slants toward the axle means. The roller means includes a plurality of rollers each conically shaped with an exterior surface positioned substantially tangentially proximate the arcuate recessed surface.

The pump head means preferably has a central member for connection to the axle. A top member is connected to the central member with a handle rotatably connected thereto and moveable between the first position in which the handle extends away from the pump head means and is operable by the user to rotate the pump head means and a second position in which the handle is positioned in a stored configuration proximate the top member.

In yet another arrangement, the pump head means includes a base member secured to the central member and the roller means is a pair of rollers positioned substantially diametrically opposite each other between the top member and the base member. The lock member is preferably positioned in the front and operable by the user to secure the conduit means to the side of the throat. It is also preferable that the motor means be a servomotor connected to rotate the axle means.

The inlet detecting means of the extracorporeal support system includes an interconnect section for interconnection in the conduit means. An aperture is formed in the interconnect section with a membrane sealingly secured thereto over the aperture for movement inwardly and outwardly with respect to the aperture. A housing is sealingly secured to the interconnect section over the aperture and filled with a liquid. A plunger is positioned within the housing and operable between the first position in which it is in contact with the membrane urging it into the interconnect section and a second position in which it is spaced away from the membrane. The solenoid is positioned proximate the plunger and operable to move the plunger between the first and second positions. A port is also formed in the housing with a pressure sensor connected thereto to sense the pressure of the liquid in the housing as reflected by movement of the membrane to generate signals reflective thereof at its output. The interconnect section preferably has an inlet and outlet with connecting means at the inlet and the outlet for interconnection within the conduit means. The plunger desirably has an arcuate head to contact with the membrane positioned at the end of a shaft. The solenoid is positioned along the shaft. A spring is preferably positioned to urge the plunger to and away from the membrane.

The solenoid valve means may desirably be fluid flow blocking clamps having a base with a rotary solenoid secured thereto and electrically connected to receive operating signals. An axle is secured to the rotating solenoid to extend away therefrom. A frame is secured to the axle with a roller secured thereto spaced away from the axle and rotatable to a first position proximate a stationary member to clamp the conduit means positioned thereinbetween, and to a second position in which the roller is rotated away from the stationary member. The stationary member is secured to the base with the roller moving relative thereto.

A method of extracorporeal support is also disclosed in which the system components are assembled and put into operation to effect a blood support operation.

BRIEF DESCRIPTION OF THE DRAWINGS

In the drawings, which illustrate the best mode presently contemplated for carrying out the invention:

FIG. 6 is a partial perspective cut-away-view of a portion of a roller pump housing;

FIG. 7 is a cross-sectional view of a block for use with the roller pump in the configuration illustrated in FIG. 6;

FIG. 8 is a top or plan view of a key for use with the roller pump of FIG. 2;

FIG. 9 is a cross-sectional view of a pressure detector for use in the extracorporeal support system of the instant invention;

DESCRIPTION OF THE ILLUSTRATED EMBODIMENT

Figure 1:
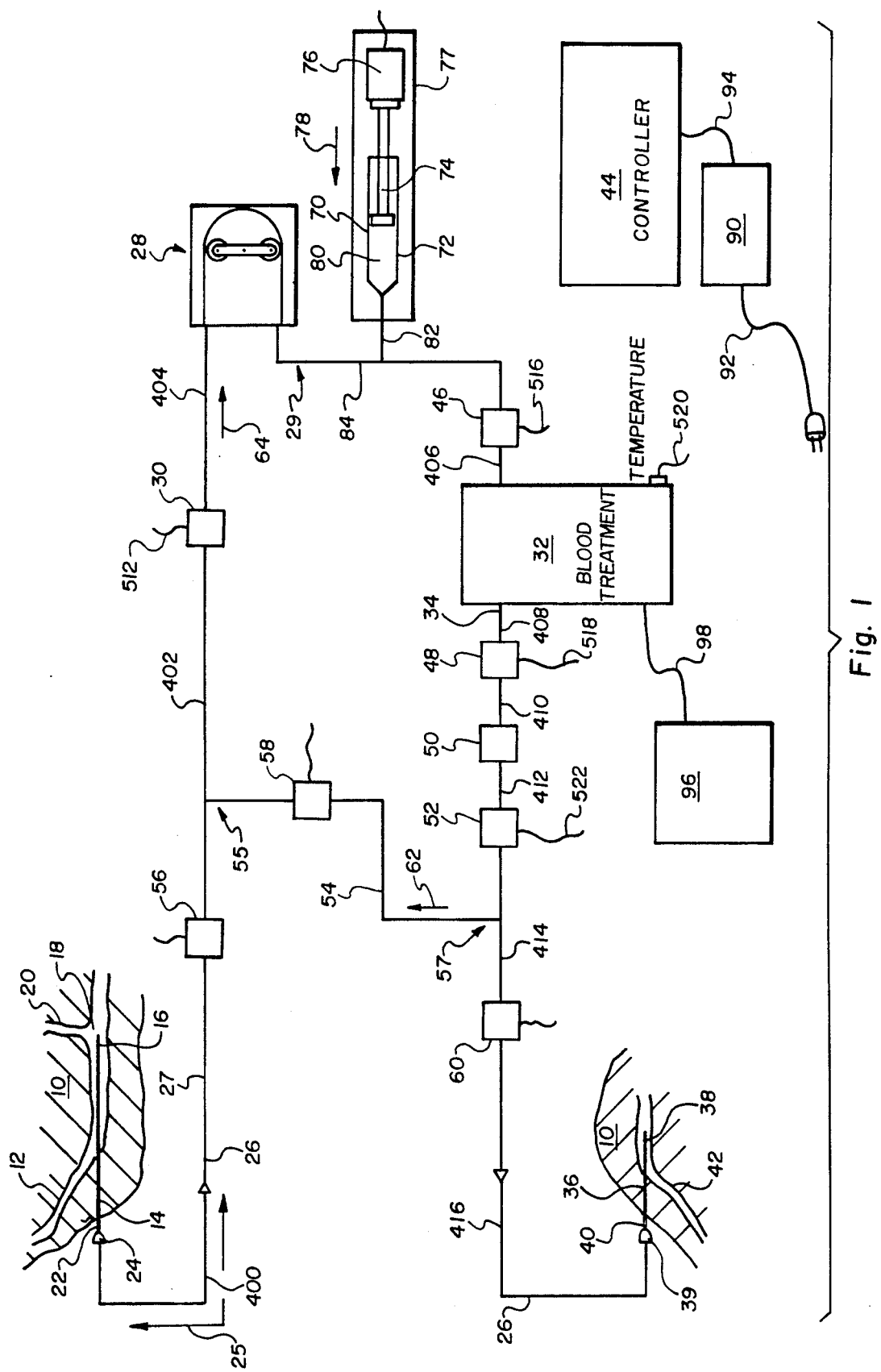
FIG. 1 is a simplified system diagram of an extracorporeal support system of the instant invention.

A block diagram representative of an extracorporeal support system is depicted in FIG. 1. The system functions to remove blood from a patient 10 more specifically from the venous system of that patient. The blood is then pumped through the system to a blood treatment device such as an oxygenator and returned to the patient 10 and more specifically to the arterial system of the patient.

In the system of FIG. 1, the blood is removed from the patient 10 and more specifically the arterial system depicted by a vein 12. Blood is removed by inlet means here shown to be a catheter 14 which is inserted into the patient so that distal end 16 of the catheter 14 is positioned preferably in the vicinity of the heart of the patient and more specifically in the vena cava or right atrium. The vena cava or right atrium 18 acts as a small bladder or reservoir into which the patient's blood may collect for direct supply to the heart via a vein 20. The blood of the patient is removed from this region via the catheter to minimize the risk of collapsing any blood vessels, to minimize abnormal flow and to minimize evacuation from any other region.

The catheter 14 has a proximal end 22 which is positioned exterior the patient with a connector 24 for interconnection to conduit means here illustrated as a hollow tube 26 to transmit the blood from the catheter 14 into the system as hereinafter further described.

The catheter 14 acts as an inlet means to receive the blood of the patient. The conduit means does not have any bladders or reservoirs formed in it or connected in it. By eliminating the bladders of the prior art, the total blood volume in the system is reduced along with the risks attendant thereto. Insertion of the distal end 16 of catheter 14 into the vena cava employs the natural venous reservoir for the system reservoir. Thus, a notable head to keep a bladder full is eliminated so a bladder or reservoir may be eliminated. Further, the selection of the vena cava or right atrium as the reservoir allows selection of a considerably shorter length 25 (e.g. about ½ meter) of inlet tube section 27. Similarly the entire conduit means maybe markedly short and in total from connector 24 to connector 39 may be about 2 meters. The short lengths of tube reduce time of travel of blood from connector 24 to connector 39 and in turn reduce the heat loss so that a preheater to reheat the blood before its return to the body is eliminated. The fewer system elements and short lengths reduce the risk of clotting, of contamination and hemolysis thereby enhancing the therapy and reducing the attendant risk of system use.

In this embodiment the conduit means is desirably flexible Tygon ® tubing or other medically acceptable flexible tubing of substantially constant diameter to transport the blood throughout the entire system. As here illustrated, the conduit means, more particularly, the tube 26 is comprised of numerous segments between various components which are either connected to or interconnected in the tube 26 as more fully discussed hereinafter.

The system of FIG. 1 includes a roller pump means which is roller pump 28. It has the conduit means and more particularly the tube 26 extending or positioned therethrough as more fully discussed hereinafter. The roller pump 28 is configured for pumping blood through the tube 26 and is preferably driven by motor means.

Inlet detecting means is interconnected in the conduit means and more particularly in the tube 26 between the catheter 14 and the roller pump 28. The inlet detecting means as here illustrated is a pressure detector 30 which detects the pressure of the blood in the tube 26 and supplies signals reflective of the inlet blood pressure in the tube 26 to the control means 44.

The system of FIG. 1 includes blood treatment means 32 interconnected in the tube 26 downstream of the roller pump 28. The treatment means treats the blood and supplies the blood 34 through its outlet to outlet means. The outlet means, as illustrated in FIG. 1, is a catheter 36 similar to catheter 14 having a distal end 38 and a proximal end 40. The distal end 38 is positioned in the arterial system 42 of the patient 10 and preferably in the aorta proximate the heart. The proximal end 40 is connected to the tube 26 at connector 39 to receive the blood from the output of the blood treatment means 32. Thus, the blood is received by the system through the inlet means and urged through the system and through the treatment means for eventual return through the outlet means to the patient from which the blood was extracted by the roller pump means.

The system of FIG. 1 further includes control means which is controller 44 interconnected to the inlet detecting means and more particularly the pressure sensor 30 by a conductor (not shown for clarity) to receive signals reflective of the inlet blood pressure. The controller 44 is also connected to the motor means (not shown for clarity) of the roller pump means and more particularly roller pump 28 to supply operation signals thereto. The controller 44 supplies the operation signals to vary the motor speed between a stop condition in which the motor is stopped upon the receipt of a signal from the inlet detecting means and reflective of a preselected "low" inlet blood pressure and a preselected high speed upon receipt of a signal from the inlet detecting means reflective of a preselected "high" inlet blood pressure.

In effect the pressure sensor is positioned proximate the inlet 64 of the roller pump 28 to sense the pressure immediately upstream from the roller pump 28. The inlet pressure is thus transmitted to the controller 44 which varies the speed of the roller pump 28 to control the pressure sensed by the pressure sensor 30 about a preselected pressure which is selected by the user so that the volume of blood available in the patient 10 is not exhausted accidentally and so that the blood flow in the system will be relatively constant. At the same time, the pressure detector 30 acts as a guardian to preclude accidental excessive evacuation of blood from the patient by sending signals to the controller, which in fact then regulates the roller pump 28 to either speed up or slow down as necessary to maintain the blood pressure in the tube 26 and in turn in the atrium or vena cava 18 within desired parameters selected based on the patient being treated.

The system of FIG. I further includes an upstream pressure detector which is pressure sensor 46 and a downstream pressure detector which is pressure sensor 48. Both the upstream pressure sensor and downstream pressure sensor are conductively connected to the control means by conductors (not shown for clarity) to supply signals reflective of the pressure upstream of the blood treatment means and downstream of the blood treatment means respectively to the control means 44. In FIG. 1, the controller receives the signals from the upstream pressure sensor 46 and downstream pressure sensor 48 causing the controller to visually display upstream and downstream blood pressures for the user and to generate an alarm when either or both differ from a preselected setting.

The system of FIG. 1 also includes a filter 50 interconnected in the tube 26 downstream of the downstream pressure detector 48 to filter the blood before it returns to the patient to avoid accidental transmission of any material from the blood treatment means to the patient.

In FIG. 1 an air detector 52 is interconnected in the conduit 26 downstream of the filter 50. The air detector 52 detects the presence of air in the conduit means and generates a signal reflective thereof. More particularly it detects the presence of air bubbles in the blood and sends a signal reflective of their presence via a conductor (not shown for clarity) to the controller 44.

The system of FIG. 1 also includes a shunt 54 which is interconnected in the conduit means between the inlet side of the pump 28 and the outlet side of the pump 28. More particularly the shunt 54 is interconnected in the tube 26 at one end 55 between the catheter 14 and the inlet detecting means 30 and more particularly the inlet pressure sensor 30. Similarly, the other end 57 of the shunt 54 is interconnected in the tube 26 between the air detector 52 and the catheter 36. A first solenoid valve means and more particularly a flow blocking device 56 is positioned between the inlet catheter 14 and shunt 54. A second solenoid valve means and more particularly a flow blocking device 58 is positioned in the shunt 54. A third solenoid valve means and more particularly a flow blocking device 60 is positioned between the shunt 54 and the outlet means or outlet catheter 36.

Upon receipt of a signal from the air detector 52 indicating the presence of air in the blood in route to the outlet catheter 36, the controller 44 generates operating signals to operate the first, second and third solenoid valve means and more particularly the flow blocking devices 56, 58 and 60 so that the flow blocking device 56 moves from its normally open operating position to a closed position. Similarly, flow blocking device 58 receives its operating signal from the controller 44 to move from its normally closed condition to an open condition in which flow through the shunt 54 is permitted. At the same time the third flow blocking device 60 moves from a normally open position, in which blood flows through the tube 26 to the catheter 36, to the closed condition. Therefore, the pump 28 urges blood through the blood treatment device 32 and through the shunt 54 in the direction of arrow 62 and back to the inlet of the pump 28 as indicated by arrow 64. This condition is maintained until the signal from the air detector 52 indicates that there is no air present in the tube 26, causing the first, second and third flow blocking devices to return to an operating configuration in which the first and third flow blocking devices 56 and 60 are open and the second flow blocking device 58 is closed to interrupt flow through the shunt 54. The air detection feature is intended to avoid introducing air accidentally into the patient and thereby causing an embolism, with the related risks of damage to the patient.

The system of FIG. 1 may further include a second pump means interconnected into the tube 26 for metering fluids into the blood in the tube 26. In the system of FIG. 1, the second pump means is a syringe 70 having an outer casing 72 and a piston or plunger 74 which is mechanically connected to a motor device 76. In operation the motor 76 moves the plunger 74 inwardly 78 to meter fluids held within the syringe 70 through tube section 82 into the tube 26 between the output 29 of the roller pump 28 and the upstream pressure sensor 46. The motor device 76 is interconnected to control means 44 by a conductor (not shown for clarity) so that the device 76 may be operated to meter at a rate desired by the user. It may be noted that the motor device 76 may be a solenoid or any other electrical device that would provide linear motion of sufficient force to drive the plunger 74 inward and in turn urge the fluid 80 through the tube section 82 into the tube 26 and more particularly the tube section 84 of tube 26 between the pump outlet 29 and the upstream pressure sensor 46.

It may be noted that the controller 44 has a power supply 90 interconnected therewithin to receive power from an external source here illustrated to be 115 volt power from a conventional wall plug via conductor 92. The power supply 90 in turn supplies power via conductor 94 throughout the controller 44.

It may be also noted that the blood treatment means 32 may preferably be an oxygenation device which is connected to receive oxygen from a supply thereof 96 via a tube 98. That is, the blood treatment means 32 may be a membrane structure which receives the supply of oxygen and supplies the oxygen to the blood passing therethrough. Other types of blood treatment devices may also be suitable as more fully discussed hereinafter.

Roller Pump

Figure 2:
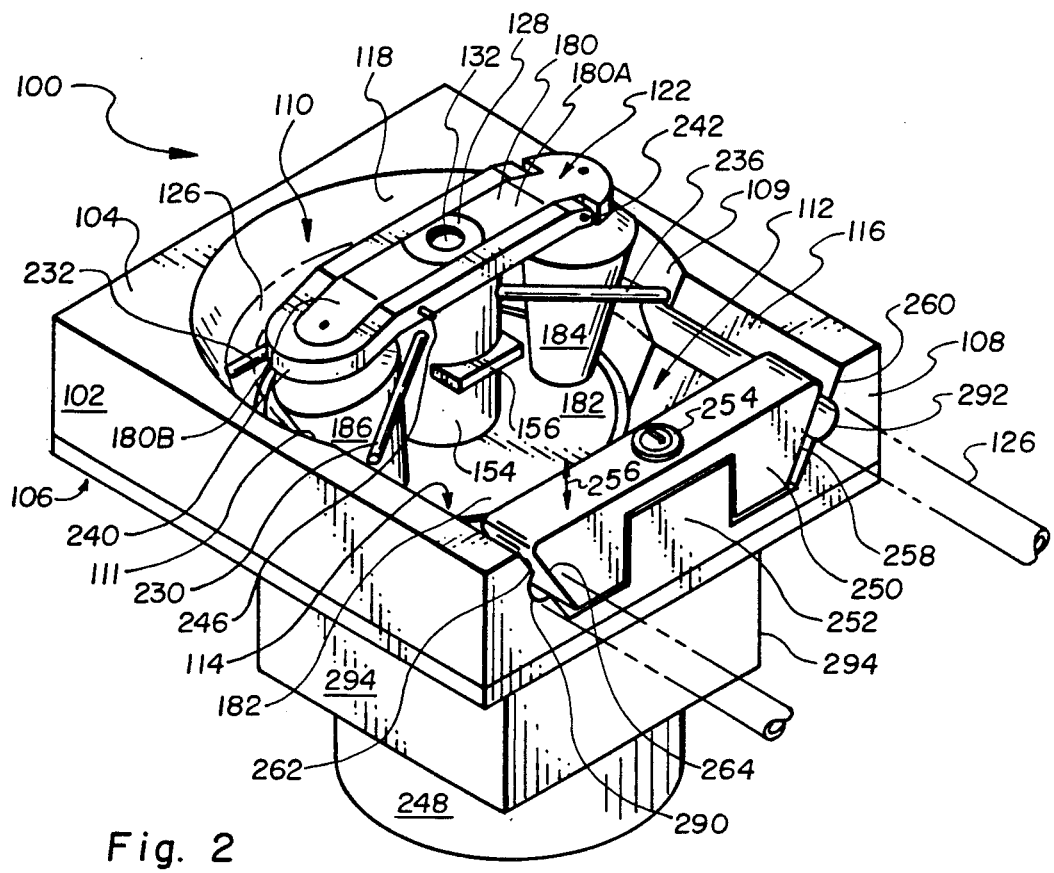
FIG. 2 is a perspective view of a roller pump for use in an extracorporeal support system of the instant invention.

FIGS. 2 through 5 illustrate the pump arrangement particularly suitable for use in the system of FIG. 1. In FIG. 2, a roller pump 100 has a housing 102 formed with a top 104, a bottom 106 and a front 108. The housing 102 has a keyhole-shaped recess 110 formed in the top 104 extending inwardly into the housing 102. The recess 110 has a throat 112 which has opposite sides 114 and 116. The opposite sides 114 and 116 open through the front 108 and extend into the housing 102 to connect with opposite ends 109 and 111 of an arcuate recessed surface 118.

The pump 100 has axle means rotatably secured to the housing 102 to extend into the recess 110. More particularly, the axle 120 (FIG. 4) extends into the housing 102 and more specifically into the recess 110 to be centrally positioned within the recess 110 with respect to the arcuate recessed surface 118.

The pump 100 may be regarded as having a pump head means which is removably secured to the axle means and positioned within the recess 110. As illustrated in FIG. 2, the pump head means may include roller means positioned proximate the arcuate recessed surface 118 for urging conduit means and more particularly tube 26 against the arcuate recessed surface 118.

Figure 4:
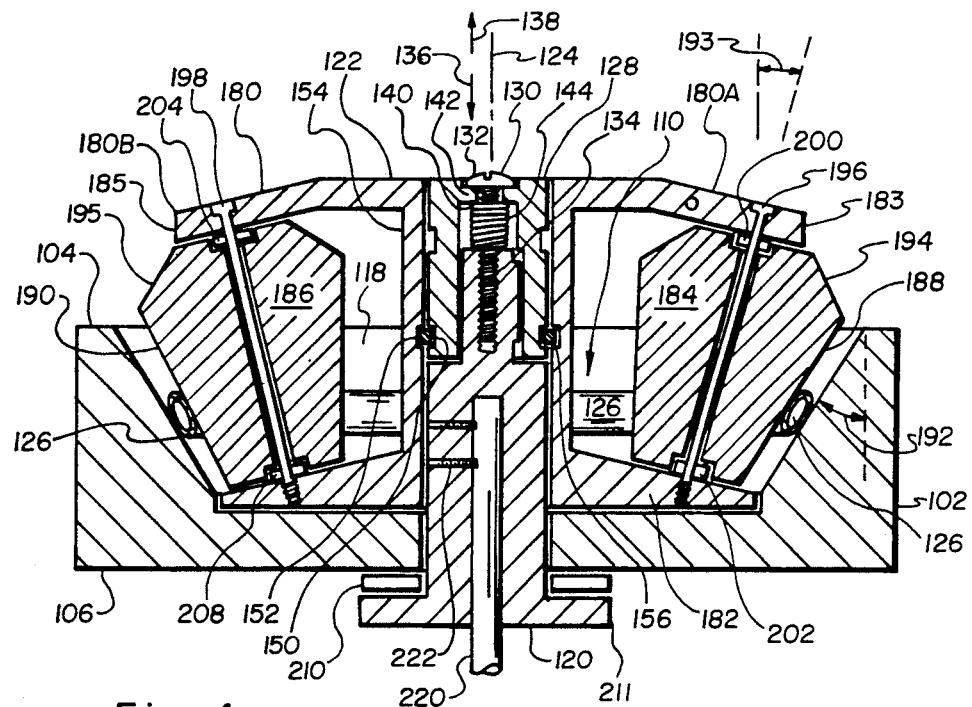
FIG. 4 is a cross-sectional view of the roller pump of FIG. 2.

Referring specifically to FIG. 4, the pump head 122 is shown to include locking means for removably securing the pump head 122 to the axle 120. The locking means includes an engagement portion and a latch member positioned for operation by the user and operable between a first position in which a latch member engages the engagement portion to secure the pump head to the axle 120 and a second position in which the latch member is disengaged from the engagement portion removably from the axle as more fully described hereinafter.

The pump of FIG. 4 further includes an adjustment structure interposed between the pump head 122 and the axle 120 for moving the pump head means 122 axially 124 toward 136 and away 138 from the axle 120 to in turn adjust the degree of pressure being exerted on the tube 126 and in turn the degree of volume of fluid being pumped through the tube 126. That is, operation of the adjustment structure causes the roller means to move toward and away from the arcuate recessed surface 118 and in turn adjust the degree of squeeze or pressure being exerted against the tube 126 and further the volume output of the pump.

The adjustment means shown in FIG. 4 includes a follower 128 positioned to move toward and away from the axle 120. The adjustment means includes a screw arrangement 130 which has a head 132 accessible to the operator with threaded portions 134 interconnecting the follower 128 to the axle 120 to move the follower toward 136 the axle 120. In operation, the head 132 is rotated by the user by the use of, for example, a screwdriver. Operating the head 132 in the outward direction allows the spring 144 to contact lip 142 to urge the follower 128 outwardly away from the axle 120.

In reference to the locking means, it can be seen in FIG. 4 that an engagement portion is formed in the follower 128. More particularly, a slot 150 is formed in the follower 128 on both sides thereof as shown. Similarly, corresponding slot 152 is formed in a sleeve section 154 of the pump head 122. A key 156 slides into the key way or opening formed by the slots 152 and 150 which are positioned with respect to each other to form the key way.

The key 156 is best shown in FIG. 8. The key has a tongue portion 160 which extends outwardly away from the sleeve 154 for operation by the user. The key 156 fits within the key way formed by the slots 152 and 150 as stated before. The slot 150 in the follower 128 is shown in dotted line in FIG. 8.

The key 156 is formed to have a keyhole-shaped opening 162 having a throat portion 164 and a circular or larger opening section 166. It can be seen the arcuate or circular section 166 has a cross-section which in diameter 167 exceeds the diameter 169 of the follower 128. Accordingly, when the key 156 is positioned in the unlock condition with the larger portion 166 centrally about the follower 128 as illustrated in FIG. 8, the entire pump head 122 may be moved upwardly, leaving behind the follower 128 and the axle 120. When the key 156 is positioned in the lock condition as shown in FIG. 8 the throat portion 164 is urged into the key way and in particular the slot 150 so that relative movement is prevented. The external portion 168 interacts with the slot 152 while the internal portion 170 of the throat 164 interacts with the slot 150, to act in total to prevent relative movement between the key way and the follower 128 and thereby locking the pump head 122 to the follower 128 and in turn to the axle 120. The key 156 may have ears 172 and 174 to prevent excessive movement of the key 156 in an unlocking configuration. Alternately, the key 156 may be formed to snugly fit into the slot 152 of the sleeve 154. The key 156 may be sized so the outer edge 168 of the key 156 may fit snugly against the exterior outward surface of the slot 152. In turn, the key 156 will remain secure in the sleeve 154 upon removal of the pump head 122 from the follower 128.

Further, it may be noted that the pump head 122 has a top member 180 and a base 182 interconnected by the sleeve 154. As better seen in FIGS. 2, 3 and 4 the top member 180 is an elongated section extending transversely and substantially symmetrically away from the follower 128. The upper member 180 has opposite halves 180A and 180B which are positioned to extend opposite from each other in a substantially symmetric pattern to function as a transverse member or arm. The upper member 180 is desirably secured to the sleeve 154 to rotate therewith. As best seen in FIG. 4, the upper member 180 is unitarily formed with the sleeve. Alternately, the upper member may be secured thereto by welding or other adequate mechanical securing arrangements.

As better seen in FIG. 4, the sleeve 154 is also unitarily formed with the base 182. The base may also be separately formed and attached to the sleeve 154 if desired. Also, it may be seen in FIG. 4 that the sleeve is made to snugly, but rotatably fit about the axle 120.

The rollers 184 and 186 are each secured between the base 182 and the upper member 180 at the outer ends 183, 185 of the upper member 180. The rollers are each formed to be conical in shape with an outer surface such as surface 188 positioned to be proximate the arcuate recessed surface 118 in the recess 110. Specifically, it can be seen in FIG. 4 that the outer surface 188 of roller 184 is positioned to be substantially in alignment with or substantially tangential to the arcuate recessed surface 118. The tube 126 is positioned between the outer surface 188 of the roller and the arcuate recessed surface to be pressed or urged against the surface 118 by the roller 184. Upon rotation, the roller 184 rolls over the tube 126 squeezing it as illustrated in FIG. 4 and thereby urging liquid or fluid in the tube 126 therethrough. A positive displacement pumping action is effected.

It may be noted that the recessed arcuate surface 118 is formed in the housing 102 to angulate inwardly toward the axle 120. As shown in FIG. 4, the surface 118 is positioned at a angle 192 with respect to the axle 120 and the axis 124 of the axle. Similarly, the rollers 184 and 186 are each positioned so that the outer surfaces thereof 188 and 190 each are similarly angulated with respect to the axis 120. As shown in FIG. 4 the rollers 184 and 186 are positioned at a angle 193 selected so that the outer surfaces 188 and 190 are in alignment with and substantially tangential with the recessed arcuate surface 118.

The upper portions of the rollers 184 and 186 each have an upper surface 194 and 195 which extends from the outer end 183 and 185 respectively toward the top 104 of the housing 102 to avoid a protrusion and also to facilitate positioning of the tube 126 into the recess 110.

Notably, the rollers 184 and 186 are each rotatably secured between the upper member 180 and the base 182. As shown in FIG. 4, roller 184 is rotatably positioned between upper member 180 and the base 182 by axle 196 which is inserted through the upper member 180 near its outer end 183 and threadably secured into the base 182. Interpositioned between the upper member 180 and the roller 184 and also between the base 182 and the roller 184 are wear surfaces such as bearings 200 and 202. The bearings 200 and 202 are positioned and held in place by the axle 196. Roller 186 is similarly secured by an axle 198 extending through upper member 180 into the base 182. Wear surfaces such as bearings 204 and 208 are similarly held in place by axle 198.

In FIG. 4, it is also shown that the axle 120 has a bearing or bushing 210 interpositioned between the axle 120 and the underside 106 of the housing 102. In particular the axle 120 has a flange 211 which extends outwardly to contact the bushing or bearing 210. It may be further noted that the axle 120 has a shaft 220 centrally positioned therein which is connected to the drive means for rotation. The shaft 220 is held in place by one or more set screws such as set screw 222.

Figure 3:
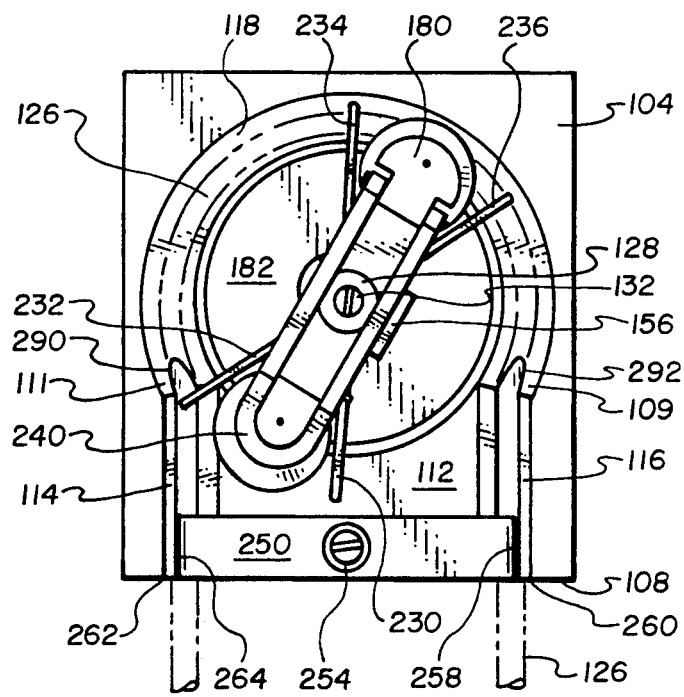
FIG. 3 is a top view of the roller pump of FIG. 2.

Referring to FIGS. 2 and 3, it can be seen that a number of fingers 230, 232, 234 and 236 extend outwardly from the sleeve 154 to which they are secured. Fingers 230 and 232 are each positioned proximate to and on opposite sides of roller 186. Similarly, fingers 234 and 236 are positioned to extend on opposite sides of roller 184. It has been found in operation that the tube 126 tends to ride upwardly or outwardly along the arcuate recessed surface 118. The fingers 230, 232, 234 and 236 are each sized to extend away from the sleeve 154 to proximate the arcuate recessed surface 118 thereby extending over the tube 126 as better seen in FIG. 3. Therefore, if the tube 126 does tend to ride upwardly or outwardly from the recess 110, it will come into contact with the fingers 230, 232, 234 and 236 to hold tube 126 in the recess 110.

Figure 5:
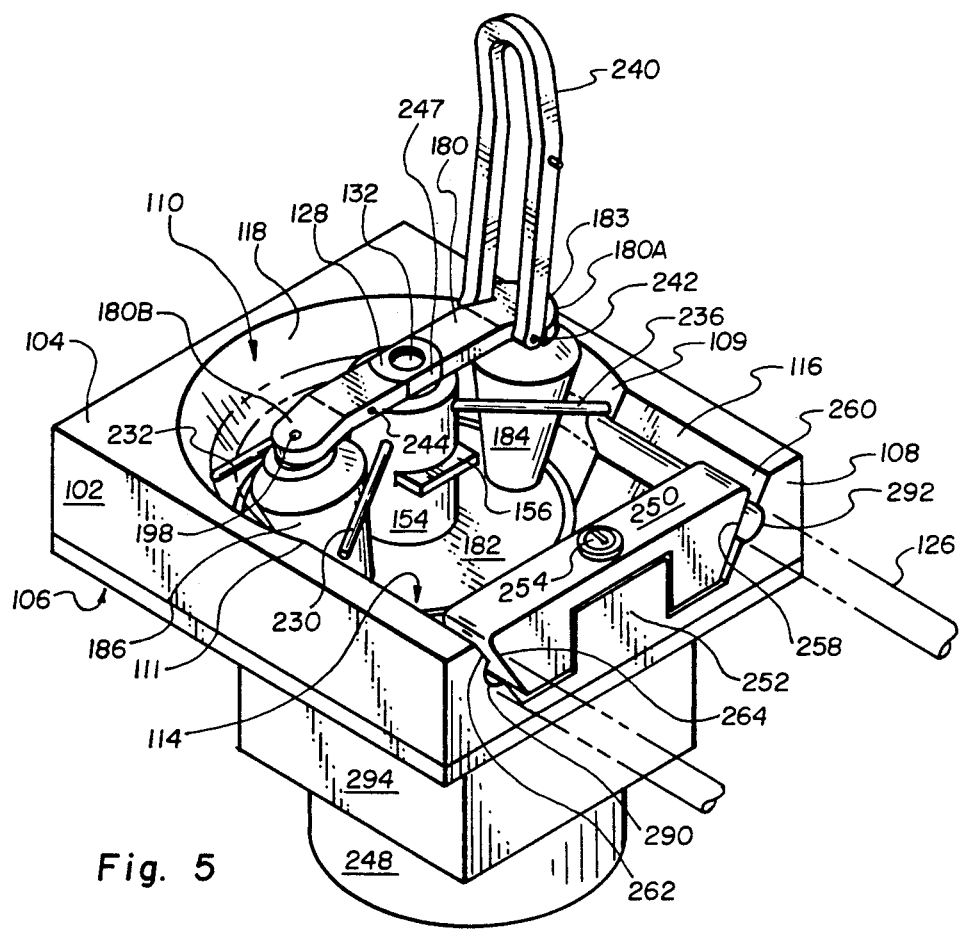
FIG. 5 is a perspective view of the roller pump of FIG. 2 in a configuration for manual operation.

The upper member 180 is here formed to have a handle 240 rotatably secured thereto to rotate between an extended position, such as that shown in FIG. 5, and a secured or stored positioned such as that shown in FIGS. 2 and 3. The handle 240 is rotatably secured to the upper member 180 by an axle or pin 242 which extends through the handle 240 and the upper member 180 and more particularly the section 180A of the upper member of 180. The handle 240 is secured to the upper member 180 by pin 246 which interconnects with an aperture 244 formed in the section 180B of the upper member 180. The handle 240 may thus be rotated between the upright position such as that shown in FIG. 5 and the secure position such as that shown in FIGS. 2 and 3. In the secure position the pin 246 will interact with the aperture 244 to secure the handle in place.

Notably, the handle 240 is "U" shaped and sized to snugly fit about the upper member 180 including the follower 128 which has a flat 247 formed to accommodate the handle 240. The handle 240 is positioned so that when extended it is spaced from the axis 124. Thus, it may be grasped by the user to rotate the pump head 122 and specifically the rollers 184 and 186 to effect pumping action manually in the event of electrical failure or component failure.

As seen in FIG. 2 the motor 248 is interconnected to a gearing arrangement 294 from which the shaft 220 extends into the axle 120. Use of a high speed servomotor 248 and a gearing arrangement 294 permits precise control of the rotation rate of the pump. A brushless dc motor model FH-BDC and a gear head FH-GB made by Robbins-Myers of Gallipolis, Ohio is presently used for the pump 100 and gearing arrangement 294.

The front 108 of the housing 102 has a block 250 positioned therein about shoulder 252. The block 250 is secured in place by a screw 254 which operates to adjust the block inwardly and outwardly 256 with respect to the housing 102. More particularly, the block 250 has an outer surface 258 which is positioned to be in alignment with the surface 116 of the throat 112. Movement of the block 250 inwardly and outwardly 256 adjusts the contact between the surface 258 and the tube 126. The surface 258 clamps or squeezes the tube 126 against the surface 116 at the outer edge 260 of the surface 116. Similarly, the block 250 operates so that its surface 264 squeezes the tube 126 against the surface 114 proximate the outer edge 262. In operation, the screw 254 can be operated to vary the degree or amount of friction or the amount of clamping action effected by the block 250 against the tube 126. Notably, the tube 126 is partially positioned within corresponding recesses 290 and 292 formed in the surfaces 114 and 116.

In FIGS. 6 and 7, an alternate arrangement is illustrated in which the housing 270 has a throat 272 with an opening 274. A track or rail 276 is positioned along the lower surface 278 in the opening 274. A block 280 has an opening 282 which is here shown to be "T" shaped and configured to slidably and snugly fit along the track 276. The block 280 is positioned over the track 276 so that its outer surface (not shown) similar to outer surface 264 of block 250 can interact against the surface 283 of throat 272 at the outer edge 284 substantially the same as illustrated in FIG. 2. The screw 286 may be used to secure the block 280 to the track 276.

It may be noted that the pump 100 has two rollers 184 and 186. It should also be understood that an arrangement with three or more rollers can be devised depending upon the pump volume required by the user at a given rotation rate.

Pressure Sensor

Referring now to FIG. 9 a pressure sensor for use in the system of FIG. 1 is illustrated. It here has an interconnect section 300 for interconnection into the conduit means and more particularly tube 26. The interconnect section 300 is here shown to have an inlet 302 and an outlet 304. However, it may only have an inlet in other applications. The inlet 302 and outlet 304 have respective flange connectors 306 and 308 for a friction connection to a flexible tube which is tube 26. An aperture 310 is formed in the interconnect section 300 with a membrane 312 positioned therein. A housing 318 is positioned about the membrane 312 and aperture 310. The housing contains a fluid 314 therewithin. Fluid pressure in the interior 316 of the interconnect section 300 is reflected to the fluid 314 in the interior of the housing 318.

Positioned within the housing 318 is a plunger 320 which operates between a first position in which it is in contact with the membrane 312 to urge the membrane 312 into the interior 316 of the interconnect section 300, and a second position where the plunger 320 is spaced away from the membrane 312. As here shown, the plunger 320 has an arcuate or mushroom-shaped head 322 with a shaft 323 extending therefrom. A solenoid 324 is positioned around the shaft 323 to urge the shaft 323 inwardly and outwardly 315 and in turn the head 322 between the first position and the second position as stated.

A spring 326 is desirably interconnected between the solenoid 324 and a flange 328 associated with the shaft 323 to urge the shaft 323 and in turn the head 322 away from the membrane 312 to a second position for normal membrane operation.

A port 330 is formed in the housing 318 to which a pressure sensor 332 is sealingly interconnected. The pressure detector 332 has a opening 334 to the atmosphere for calibration purposes. It is conductively connected via conductor 336 to an external control means such as controller 44 of FIG. 1. In use, the solenoid 324 is activated via conductor 337 to cause the plunger 320 to be urged against the membrane. In this position, the detector 332 can be calibrated since the maximum distention of the membrane is a known quantity for purposes of zeroing the sensor of FIG. 9.

In operation, the fluid in the interior 316 of the interconnect section 300 will vary in pressure and in turn cause the membrane 312 to flex inwardly and outwardly 314. These pressure variations are thus reflected at the port 330 and sensed by the detector 332. Signals reflective of the pressure variations are transmitted via conductor 336.

Clamping Device

Figure 10A:
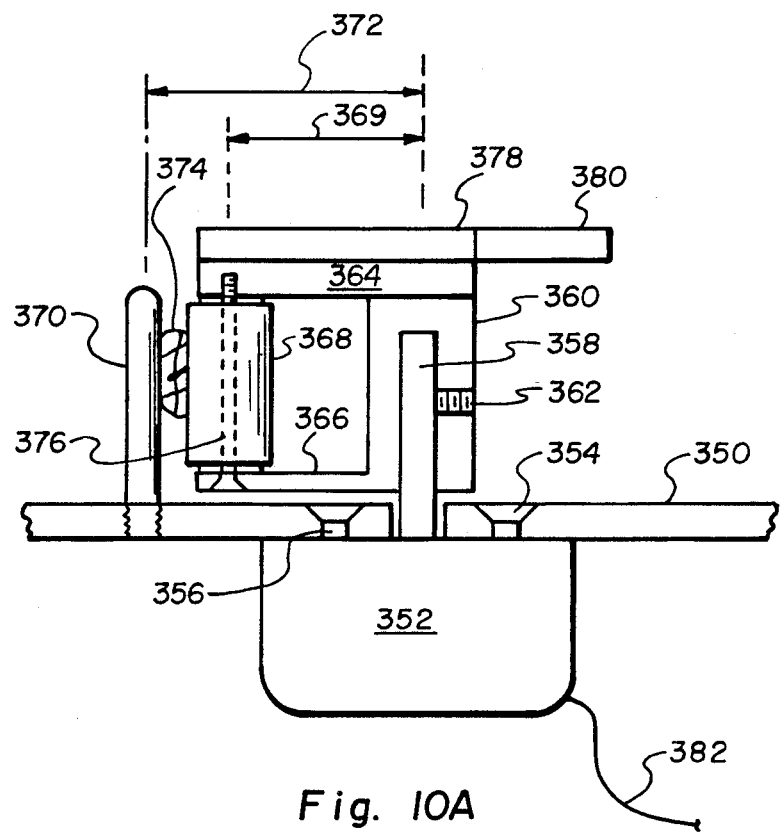
FIG. 10A is a partial cross-sectional depiction of a solenoid valve means for use in the extracorporeal support system of the instant invention.
Figure 10B:
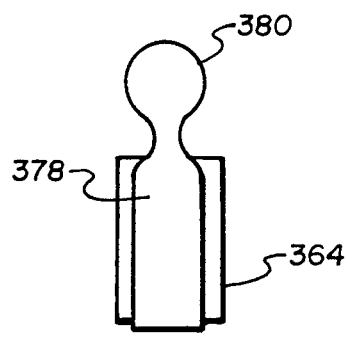
FIG. 10B is a plan view of the top of the solenoid valve means of FIG. 10A.
Figure 11:
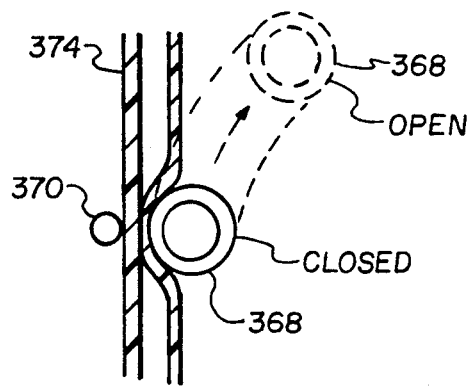
FIG. 11 is a partial cross-sectional depiction of the solenoid valve means of FIG. 10.

As noted in FIG. 1, solenoid means are used in order to block fluid flow through tubing 26. Fluid flow blocking devices 56, 58 and 60 are employed to regulate flow in the system between a normal condition and situations in which flow must be interrupted to the patient because of the detection of air by air detector 52. A number of different solenoid devices may be used. In FIGS. 10A, 10B and 11 a bridge clamp is illustrated to act as the solenoid means and more particularly the fluid flow blocking devices 56, 58 and 60 of FIG. 1.

As shown in FIG. 10A, a base 350 has a motor 352 secured thereto by screws 354 and 356. An axle 358 extends away from the motor and away from the base 358. A housing 360 is secured to the axle 358 by set screw 362 to rotate therewith. The housing 360 also has a upper member 364 secured thereto to form an upper finger 364 and a lower finger 366. A roller 368 is rotatably secured between the upper and lower fingers 364 and 366 as shown in 10A. In particular, the roller 368 is secured at a distance 369 spaced away from the axle 358 to be proximate a pin 370 which is also secured to the base 350. The tube 126 is here shown in a collapsed condition 374 interspaced between the finger 370 and the roller 368 to interrupt flow through the tube 126 also as shown in FIG. 11. That is, when the roller 368 is in the closed position as illustrated in FIG. 11 and in FIG. 10A, fluid flow through the tube 374 is interrupted because the tube 374 is effectively clamped off.

As can be seen, the finger 370 is spaced away from the axle 358 a distance 372 which is selected in relation to the distance of the roller 368 so that the clamping action will be effected when the roller 368 is put in the closed position. Upon operation of the motor 352 the clamp is rotated away from the pin 370 to an open condition. Notably, the roller 368 is rotatably secured between the fingers 364 and 366 by a shaft 376.

It may also be noted that the clamp is operable by the user by operating handle 380 which is secured to the finger 364. That is, the handle 380 has a body 376 which is secured to the upper finger 364. In the event of a electrical failure, system malfunction or failure of the motor 352 the operator may grasp the handle 380 and rotate the roller from the closed position to the open position as shown in FIG. 11.

Controller

Figure 12:
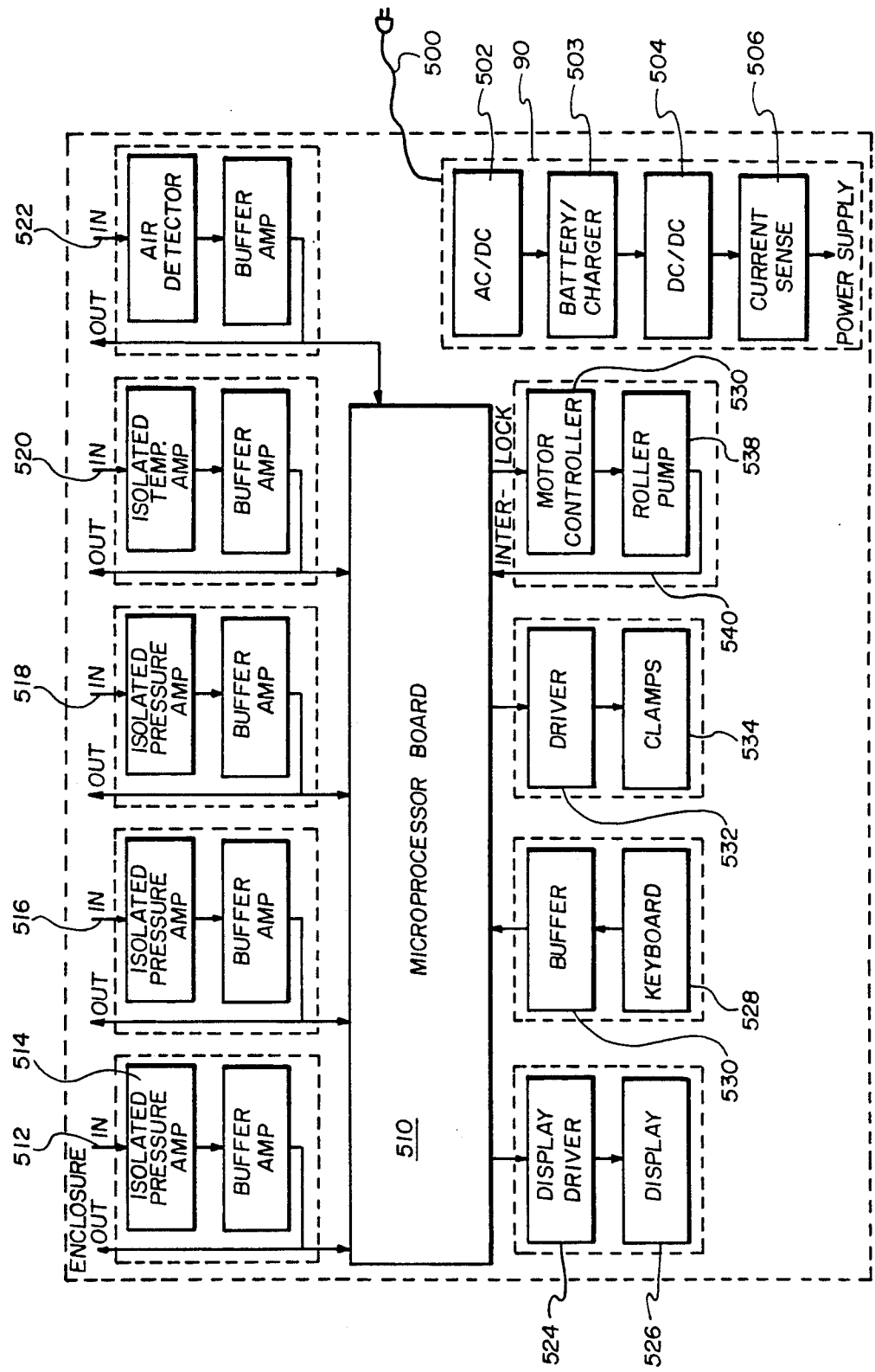
FIG. 12 is a simplified block diagram of a control means of an extracorporeal support of the instant invention.

FIG. 12 is a block diagram of the controller 44 as illustrated in FIG. 1. The controller of FIG. 1 is not shown with interconnecting conductors to the various sensors. Those conductors have been eliminated in order to clarify the illustration.

Referring to FIG. 12, a microprocessor board 510 is configured to receive an input from a pressure sensor such as pressure sensor 30 in FIG. 1 via conductor 512 through an isolating pressure amplifier 514. The input signal is then processed by a buffer amplifier as illustrated to be received by the microprocessor board 510. Similarly, input signals are received from the upstream pressure sensor 46 via conductor 516 and the downstream pressure sensor 48 via conductor 518. Signals are also received from a temperature detector via conductor 520 optionally positioned proximate to the blood treatment means 32. The signals from the air detectors may also be received via conductor 522. All the input signals are processed by respective buffer amplifiers before being transmitted to the microprocessor 510.

The power supply 90 of the controller 44 is illustrated to receive 115 volt AC power from a wall outlet via conductor 500. The power is processed through an AC to DC converter 502. The DC power is transmitted to a battery charger 503 to either an emergency battery (not shown) or a DC converter 504. The output current is monitored by sensor 506 as an excessive current drain would indicate failure of some component or a stalled pump controller. For example, FIGS. 14 through 23 show various circuits and components in which 5 volt signals are applied to operate circuits and chips within the controller 44.

Figure 13:
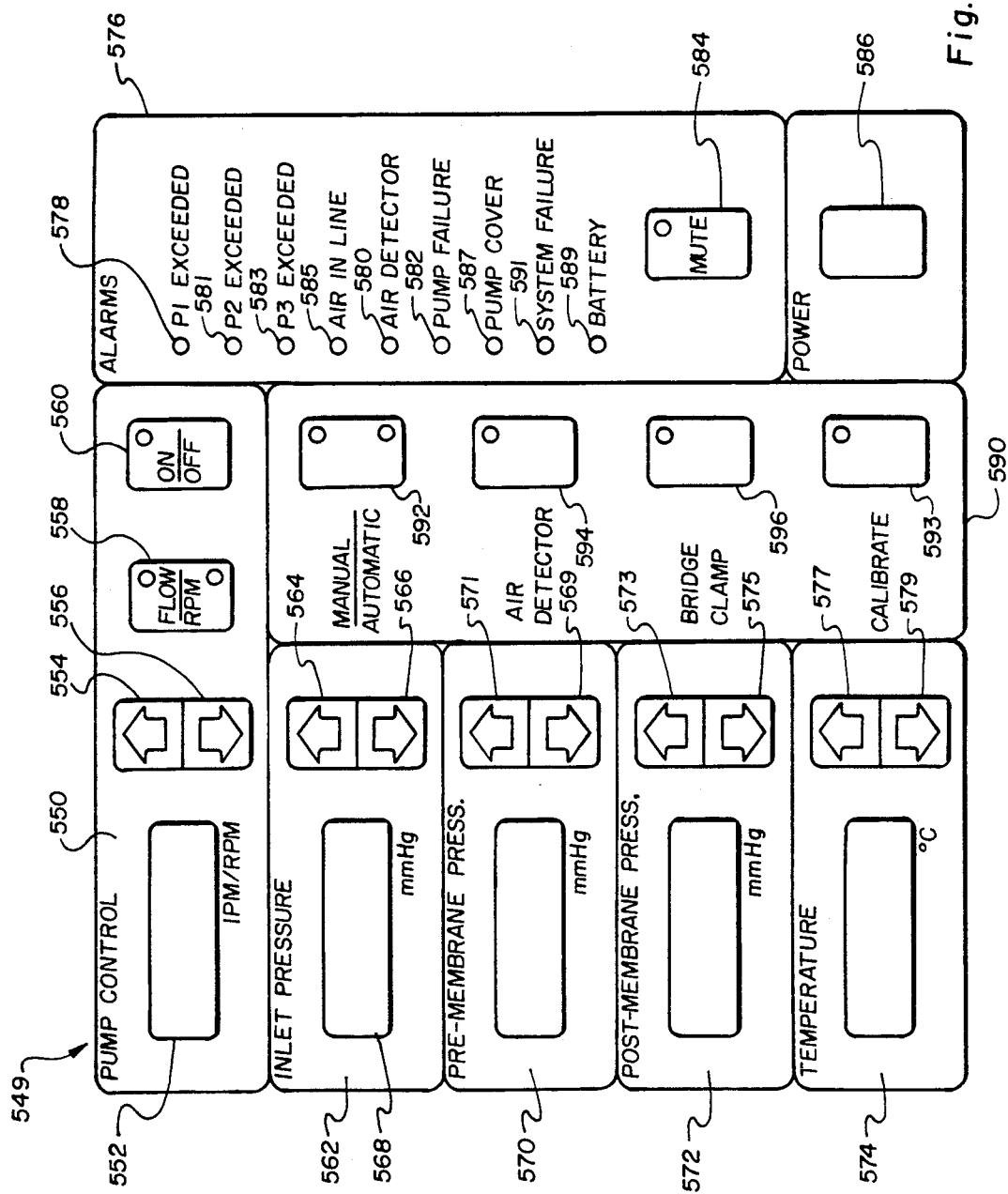
FIG. 13 is a front view of the control panel of the control means illustrated in FIG. 12 for use in the extracorporeal support system of the instant invention.

Referring again to FIG. 12 the microprocessor board 510 is shown having an output to a display driver 524 which in turn supplies the controller display 526 illustrated in FIG. 13. Similarly the microprocessor board 510 receives an input from the display of FIG. 13 and more particularly the keys or operating buttons 528 thereof through a buffer amplifier 530. The microprocessor board 510 supplies an output via driver 532 to operate the clamps 534 and more particularly the flow blocking devices 56, 58 and 60 of FIG. 1. The microprocessor board 510 also supplies an output to a motor controller 536 which in turn operates the roller pump 538. The roller pump itself supplies a feedback signal back to the microprocessor board via conductor 540.

Referring now to FIG. 13, the operation panel 549 of the controller 44 is shown configured into a series of sections. The pump control section 550 includes a indicator 552 which shows speed in revolutions per minute (RPM) or flow in liters per minute (LMP). The indication may be selected by operation of switch 558 between the flow position and the RPM position. The speed of the pump (e.g. pump 28 or pump 100) may be regulated by operating of the up switch 554 indicated by an up arrow or the down switch 556 indicated by the down arrow. Also, the pump (e.g., pump 28 or pump 100) may be turned on or turned off by operation of the activation switch 560.

The controller 44 operation panel 549 also has an inlet pressure section 562. A preselected set point pressure of the inlet pressure sensor 30 in millimeters of mercury (mmHg) is shown on the display 568. The preselected set pressure may be adjusted by operation of the up switch 564 and the down switch 566. Similarly, the control panel of FIG. 13 has a premembrane pressure section 570 which shows the set point of the upstream pressure sensor 46 that is selected by operation of the up switch 571 and the down switch 569. The pressure is displayed in millimeters of mercury (mmHg). In similar fashion, the post membrane pressure section 572 illustrates the set point of the downstream pressure sensor 48 of FIG. 1. The set point may be adjusted by operation of the up switch 573 and the down switch 575.

In operation, the temperature of the blood treatment device 32 (FIG. 1) may be indicative of its operation as well as indicative of the temperature of the blood being returned to the patient. Thus, it may be desired to position a temperature sensor proximate the blood treatment device 32 to compare the temperature (in degrees centigrade) to a set point temperature selected by operation of the up switch 577 and the down switch 579.

The control panel 549 also has an alarm section 576 which has plurality of light emitting diodes (LED's) such as LED 578 which is illuminated when the pressure of the inlet pressure sensor 30 exceeds the preselected pressure selected and shown in the display 568. Similarly, LED 581 and LED 583 show the presence of an alarm condition in the event the upstream pressure sensor 46 and downstream pressure sensor 48 sense a pressure which exceeds that indicated and preset in the displays of sections 570 and 572 respectively. The LED 585 will activate upon detection of air in the tube 26 by detector 52. LED 580 is illuminated upon deactivation of the air detector 52 by operation of switch 594 on the control panel section 590. Similarly, if the pump motor fails (e.g. motor 248, FIG. 2) LED 582 activates. A cover (not shown) may be installed over the pump in which case, LED 587 will activate in the event the pump cover is removed. A battery failure is indicated by the LED 589; and an overall system failure is indicated by the LED 591. An audible alarm may be associated with the activation of any one of the LED's above described. The audible alarm may be silenced by operation of the mute switch 584.

Power to the overall system is controlled by the "on" switch 586. The system of FIG. 1 may be manually operated or operated in automatic. In manual, the user may manually control the system by operating the pump manually through the use of handle 240 (FIG. 5) with the pump off through operation of the on/off switch 560 in the pump control section 550. The pump may also be electrically operated in the manual mode by operation of the switch 560 to the "on" condition. In the manual mode, the air detector 52 may be similarly turned on or off particularly when the system is being primed for operation. That is, in order to start up the system, air may be present in the system. Initial start up to flush out the air may be desired before connecting to the patient.

The flow blocking devices 56, 58 and 60 may also be activated or deactivated by operation of the switch 596. In some circumstances, the user may elect to place the system in a safe condition by isolating the patient from the system. In that situation the bridge clamp switch 596 may be operated. Upon operation, the flow blocking devices 56 and 60 proceed to their closed condition and flow blocking device 58 goes to an open condition. The calibrate switch 593 is used to calibrate the pressure sensor 30, the upstream pressure sensor 46 and the downstream pressure sensor 48.

Figure 14:
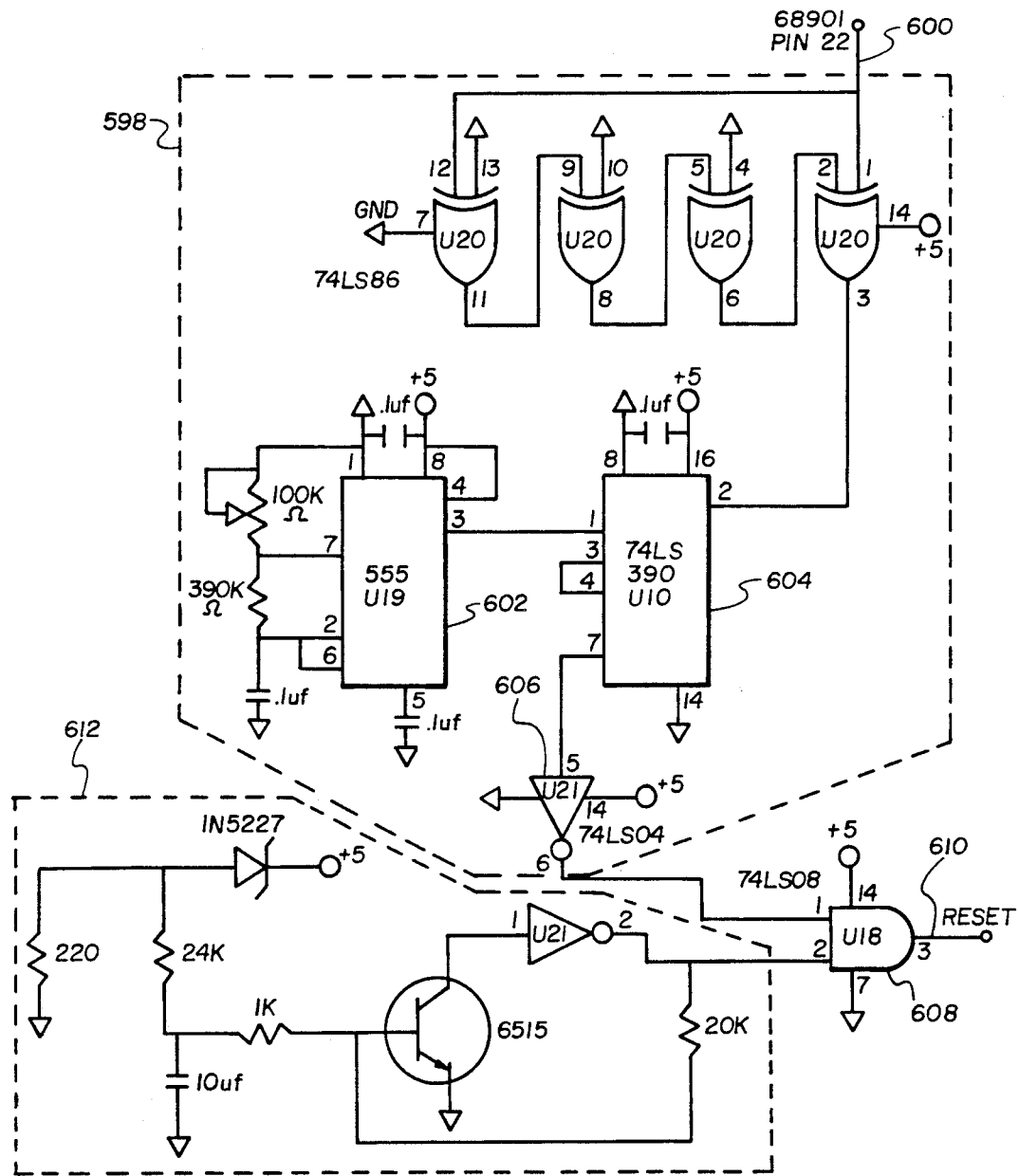
FIG. 14 is a circuit diagram of a watch-dog circuit for use in the control means of the FIG. 12.

Referring now to FIG. 14, a watch dog circuit 598 is shown connected to receive an input from a peripheral board 630 via conductor 600. The watch dog circuit 598 employs a low frequency oscillator 602. The oscillator 602 is interconnected to a buffer 604 to intermittently send signals through the inverter 606 to the "and" circuit 608 to in turn periodically supply a reset signal 610 to the microprocessor. Unless the buffer 604 is reset periodically by the microprocessor 625 via line 600, the microprocessor is reset to 0 via 610 to avoid the risk of an ambiguity where the microprocessor is locked in a cycle from which it cannot escape. The power on and reset circuit 612 is also shown in FIG. 14 supplying an input to the "and" circuit 608.

Figure 15:
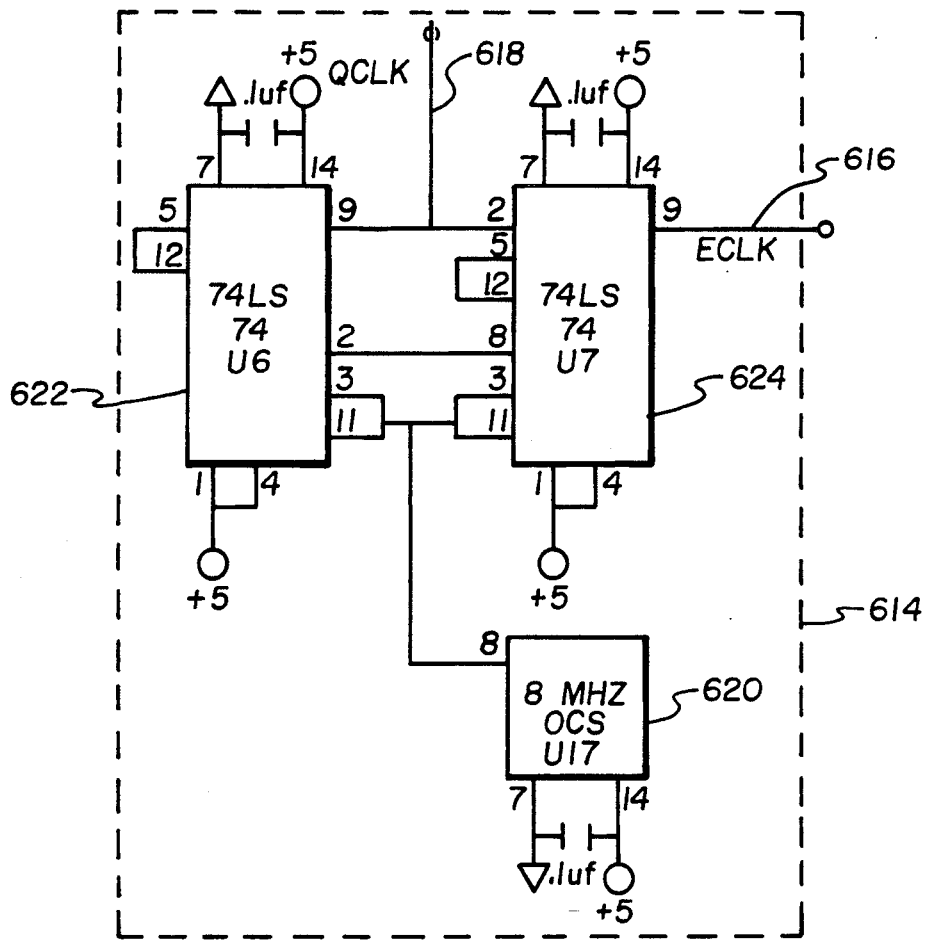
FIG. 15 is a clock circuit for use in the control means of FIG. 12.

FIG. 15 is a clock circuit which supplies a clock signal to the microprocessor. The clock circuit 614 has an oscillator 620 which supplies an output to a divider 622 and a shift and divide circuit 624. The output of the divider 622 is supplied via conductor 618 to the microprocessor. The output of the shift divide circuit is supplied to the microprocessor via conductor 616.

Figure 16:
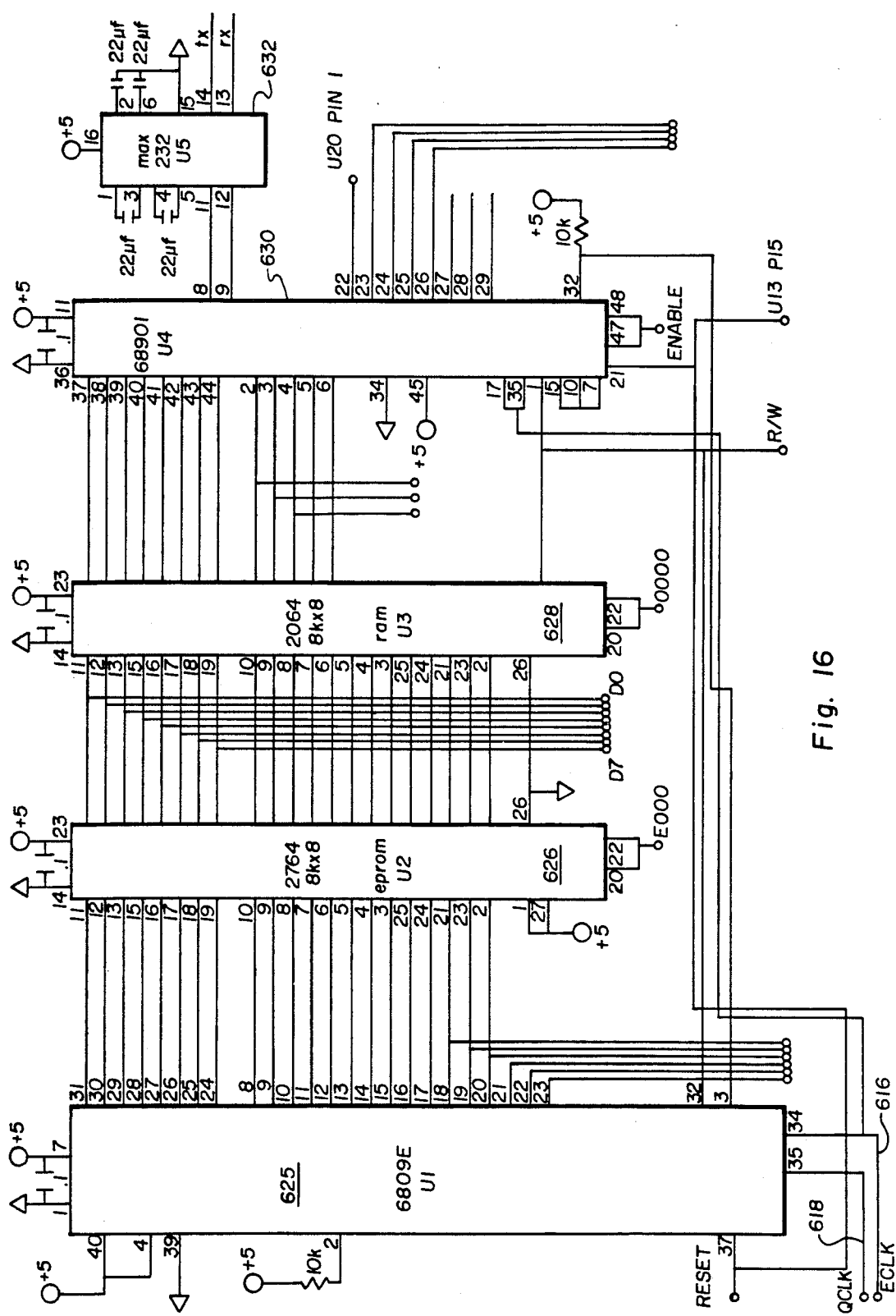
FIG. 16 is a microprocessor arrangement for use in the control means of FIG. 12.

FIG. 16 shows the microprocessor board with the microprocessor chip 625 receiving inputs from the reset circuit via conductor 610 and from the clock circuit 614 via conductors 616 and 618. The microprocessor 625 is interconnected to an eprom or erasable, programmable memory 626 and a random access memory (RAM) 628. The microprocessor chip 625 is also connected to a standard peripheral circuit 630. The peripheral circuit 630 is also connected to standard communication port 632.

Figure 17:
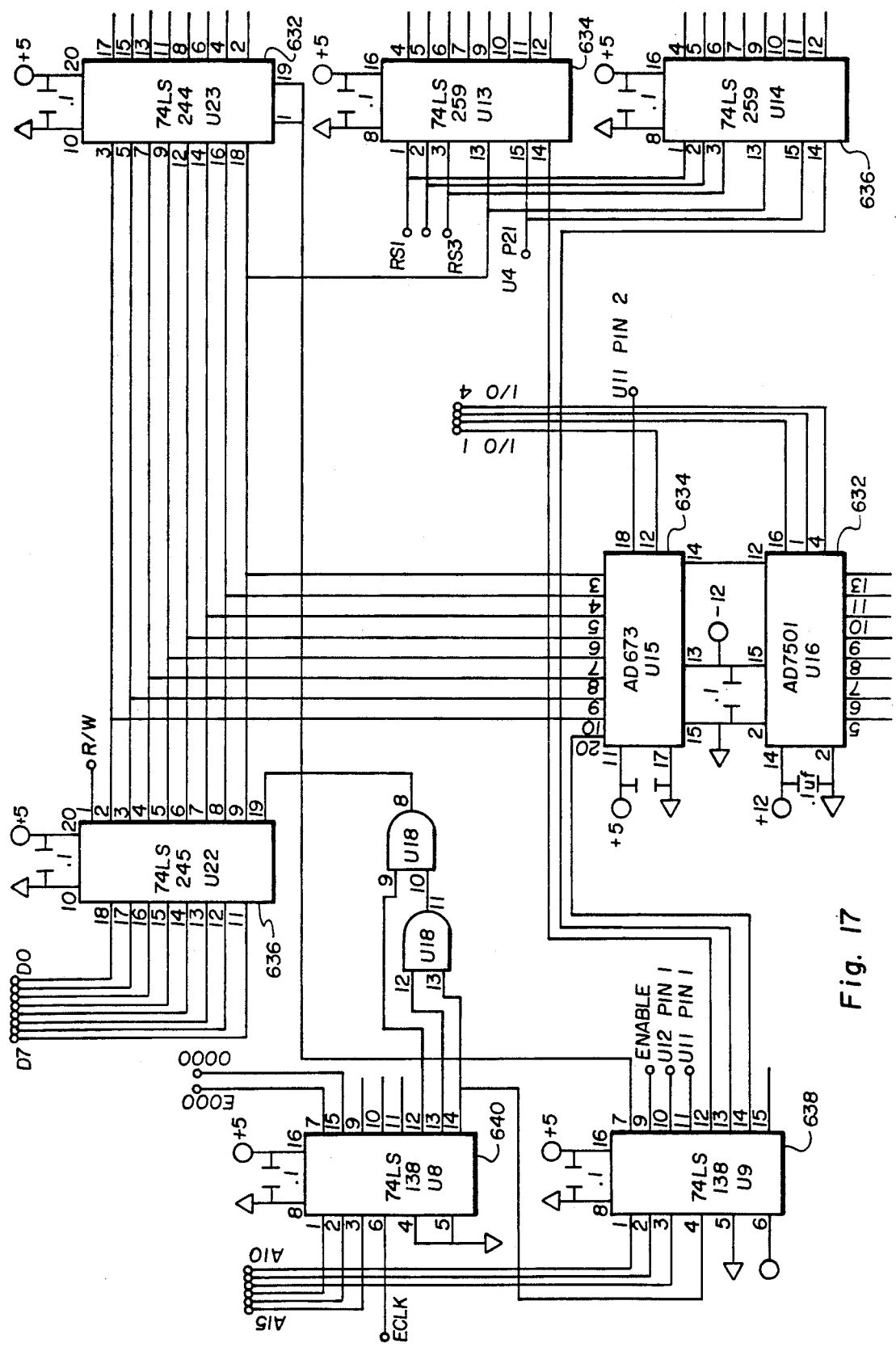
FIG. 17 is the input and output circuitry associated with the microprocessor of FIG. 16.

Referring now to FIG. 17, inputs from the pressure transducer amplifier of FIG. 12 are received by the multiplexor 632 and supplied to a single analog to digital (A/D) converter 634. The A/D converter 634 supplies its output to a bus which is controlled by a bus driver 636. The bus driver 636 processes signals to and from input/output ports such as port 632. Inputs are received by the bus driver 636 via port circuits 634 and 636 for further processing by the microprocessor. Input and output ports are selected by decoders 638 and 640.

Figure 18A:
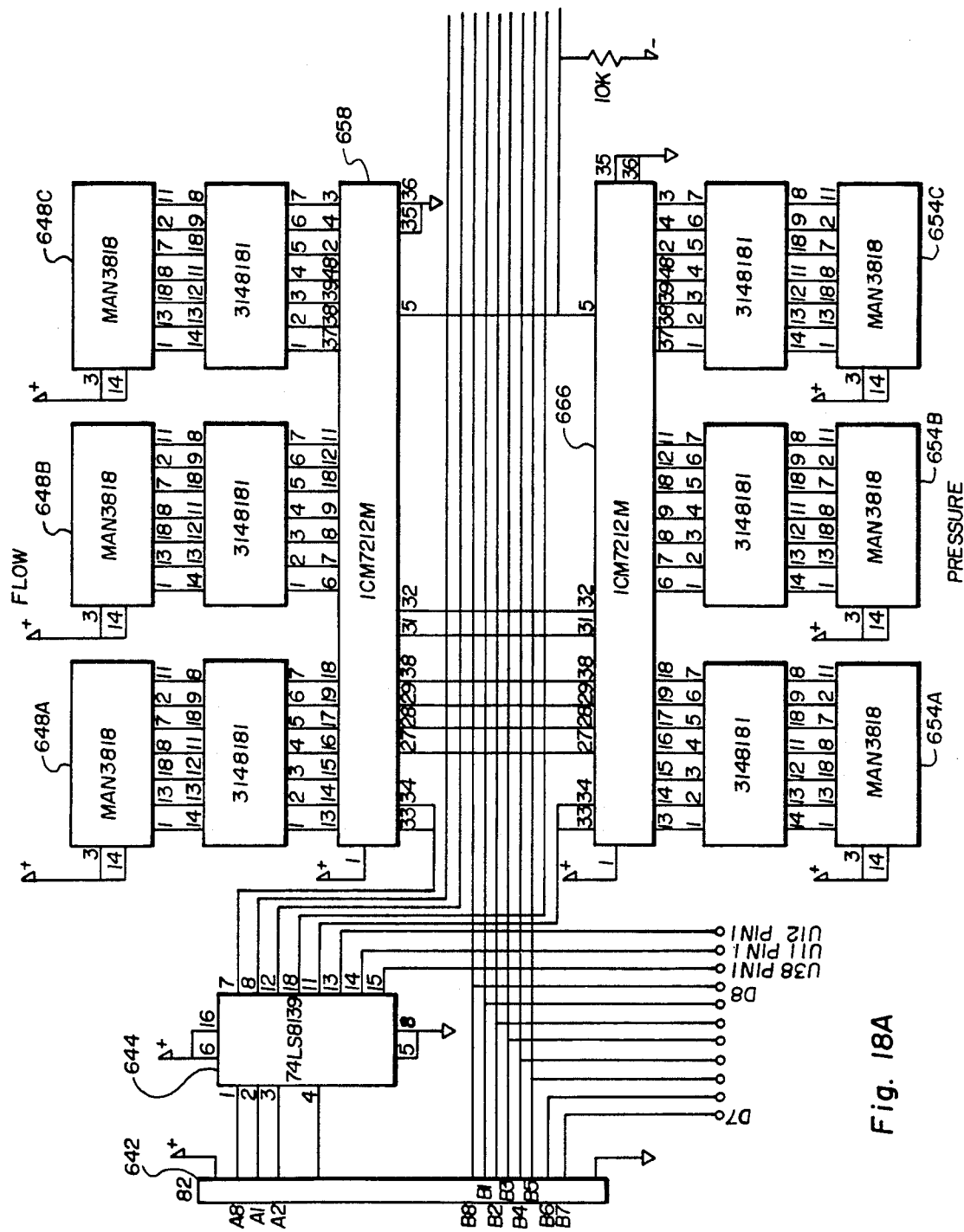
FIGS. 18A and 18B illustrate the alarm circuitry of the control means of FIG. 12.
Figure 18B:
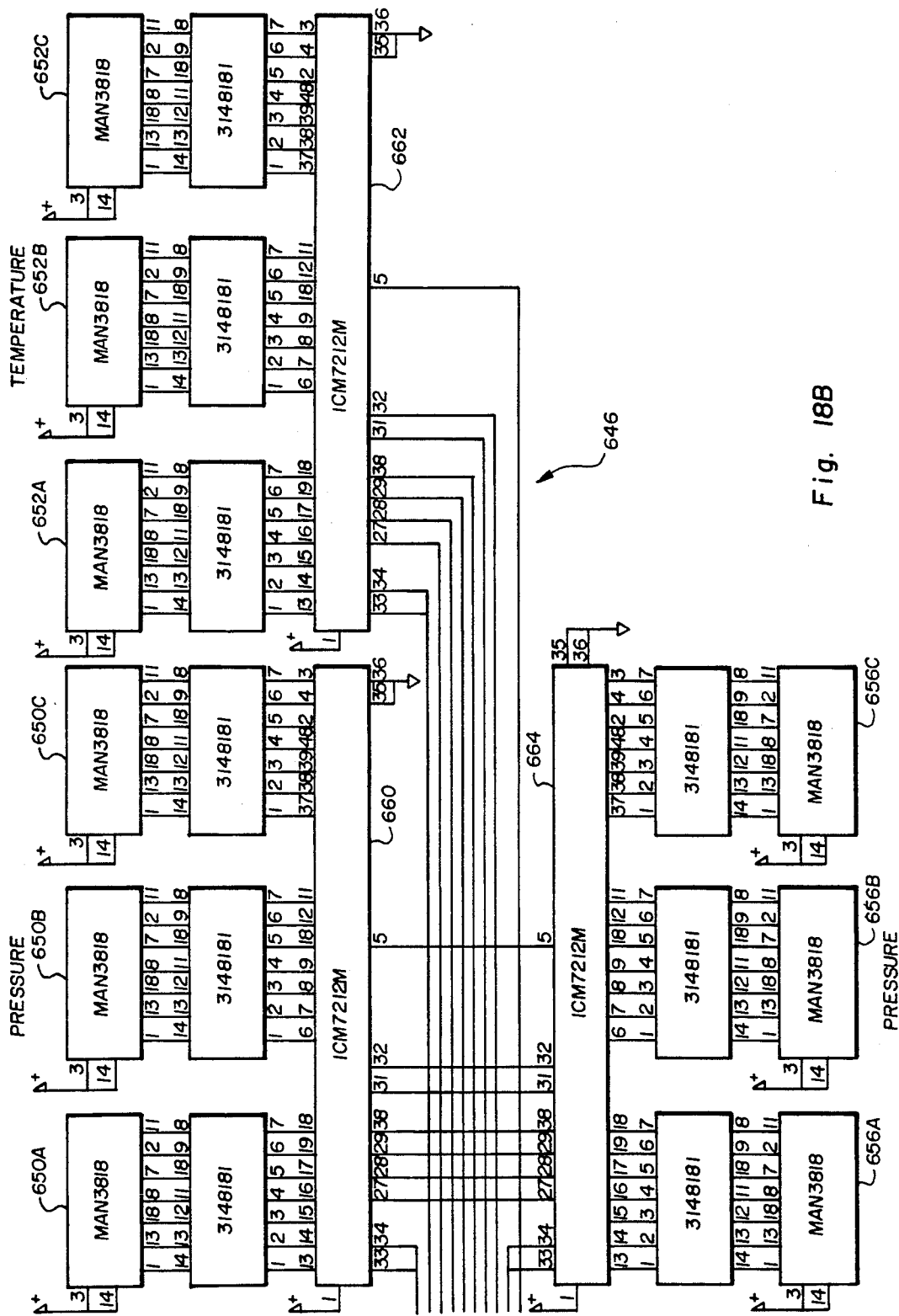

Referring now to FIG. 18, the display circuit 646 is shown with inputs from the various detectors received and supplied to various indicators which are here shown. For example, the flow indication is displayed by LED displays 648A, B, & C. Similarly, the pressure set point of the inlet pressure sensor 30 is displayed by the LED display circuits 650A, B, & C. The temperature set point of the blood treatment device 32 is displayed by LED display circuits 652A, B & C. Similarly, the pressure set point of the upstream pressure sensor 46 is shown on the LED display 654A, B, & C. The set point of the downstream pressure sensor 48 is displayed on the panel section 572 shown in FIG. 13 by LED displays 656A, B, & C. All of the LED displays 648, 650, 652, 654 and 656 are interconnected to a microprocessor-compatible LED driver 658, 660, 662, 664 and 666 respectively. Interconnected between the drivers 658, 660, 662, 664 and 666 and the LED displays 648, 650, 652, 654 and 656 are current limiting resistor banks. The LED display arrangement is interconnected by decoder 644 through a connection panel 642 further interconnected to the microprocessor.

Figure 19A:
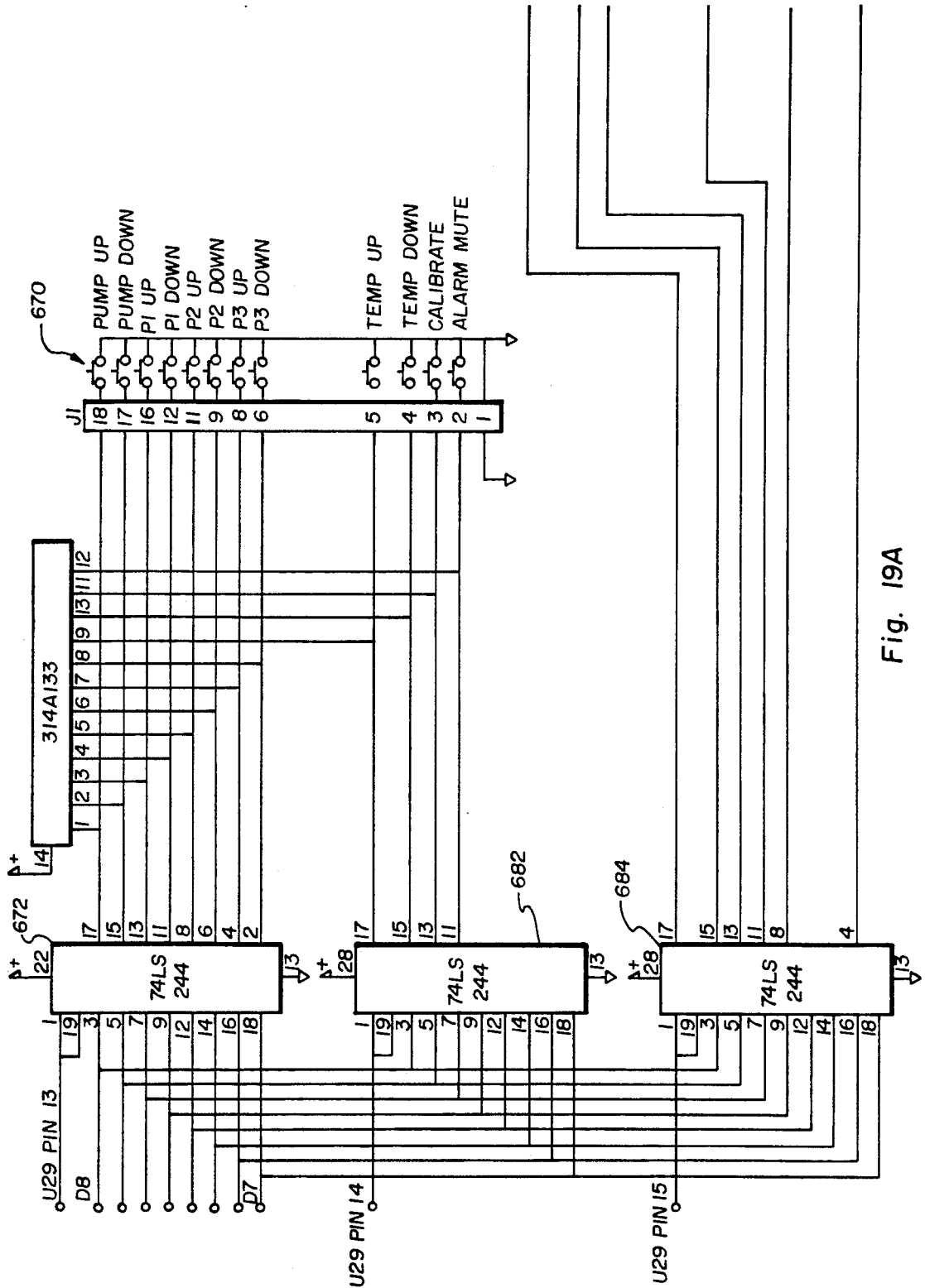
FIGS. 19A and 19B show input signal circuitry associated with the control means of FIG. 12.
Figure 19B:
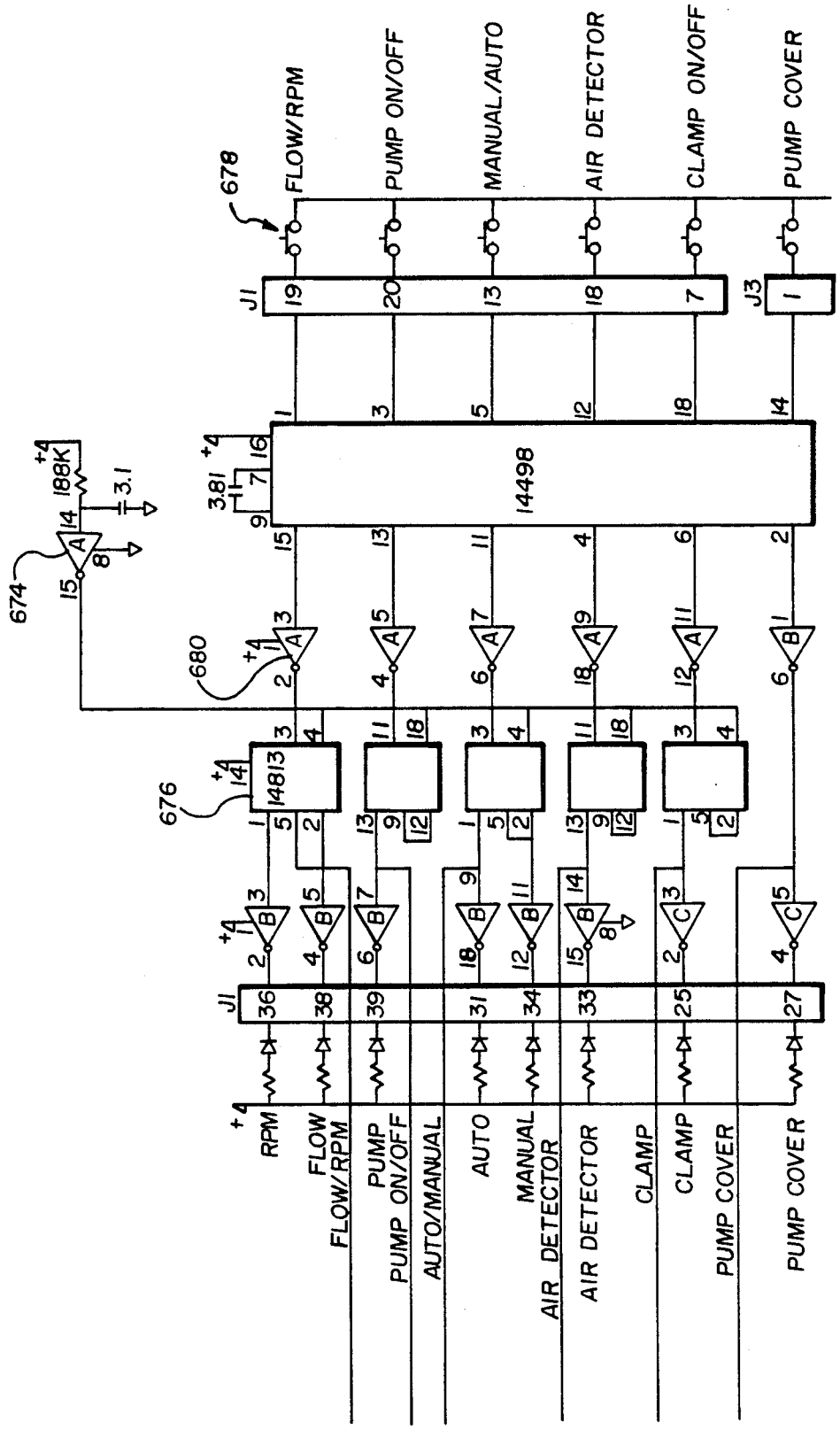

FIG. 19 shows the circuitry associated with the panel switches of FIG. 13. The switches 678 are arranged with a power-on-reset function so that upon activation, the power-on-reset amplifier 674 resets all of the latches to their normal off or on position preselected by the user. Thereafter activation of switches 678 causes operation of the inverter 680 and further activation of the latches such as latch 676. The output of the manual switches 678 is supplied through a buffer driver 684 which turns on and off to read the status of the latches 676. Similarly, buffer drivers 682 and 672 turn on and off to read the status of the switch bank 670. The output of the drivers 682 and 672 is supplied to the data bus of the microprocessor 625 (FIG. 16).

Figure 20:
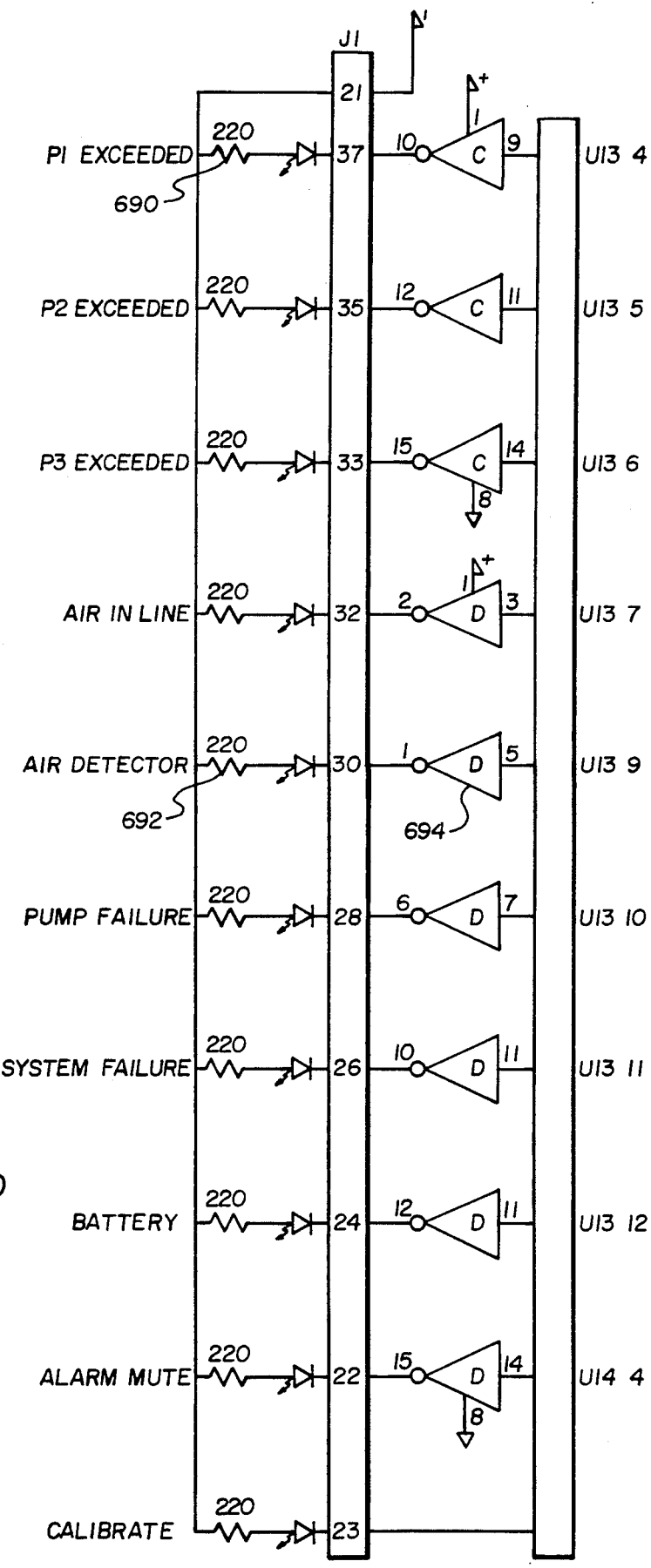
FIG. 20 shows alarm circuitry for use in the control means of FIG. 12.
Figure 21:
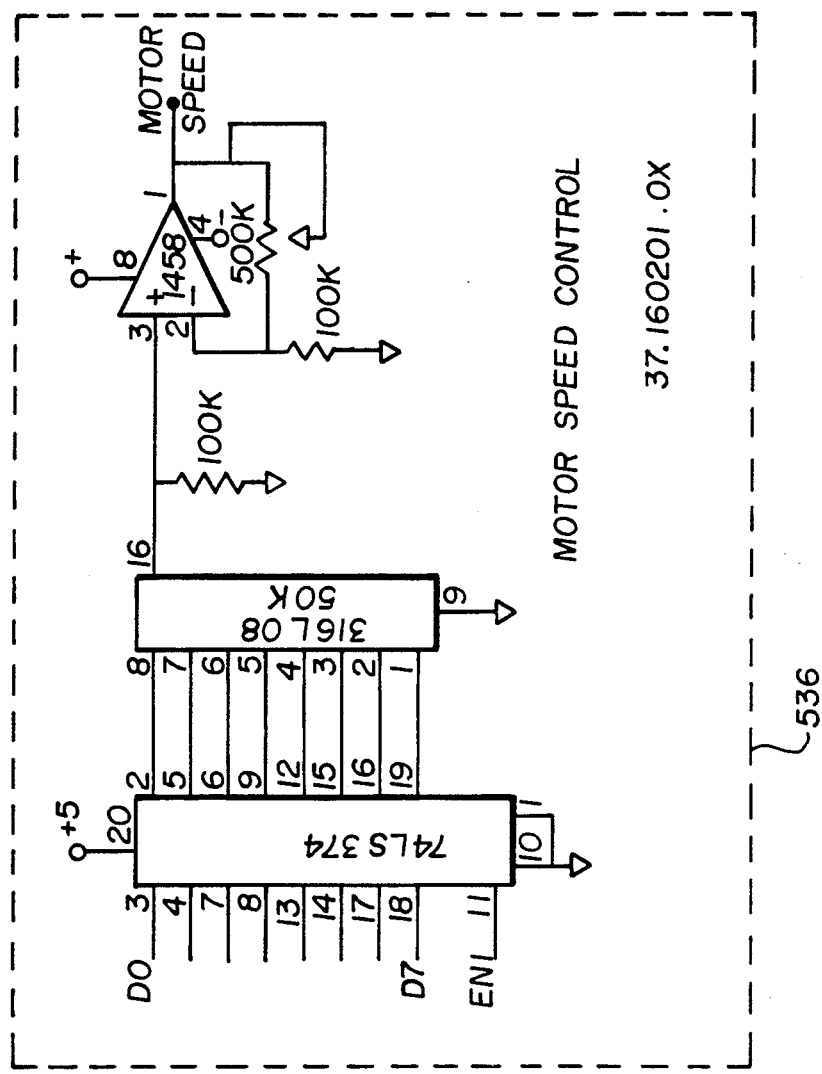
FIG. 21 shows a motor speed control for use in the control means of FIG. 12.
Figure 22:
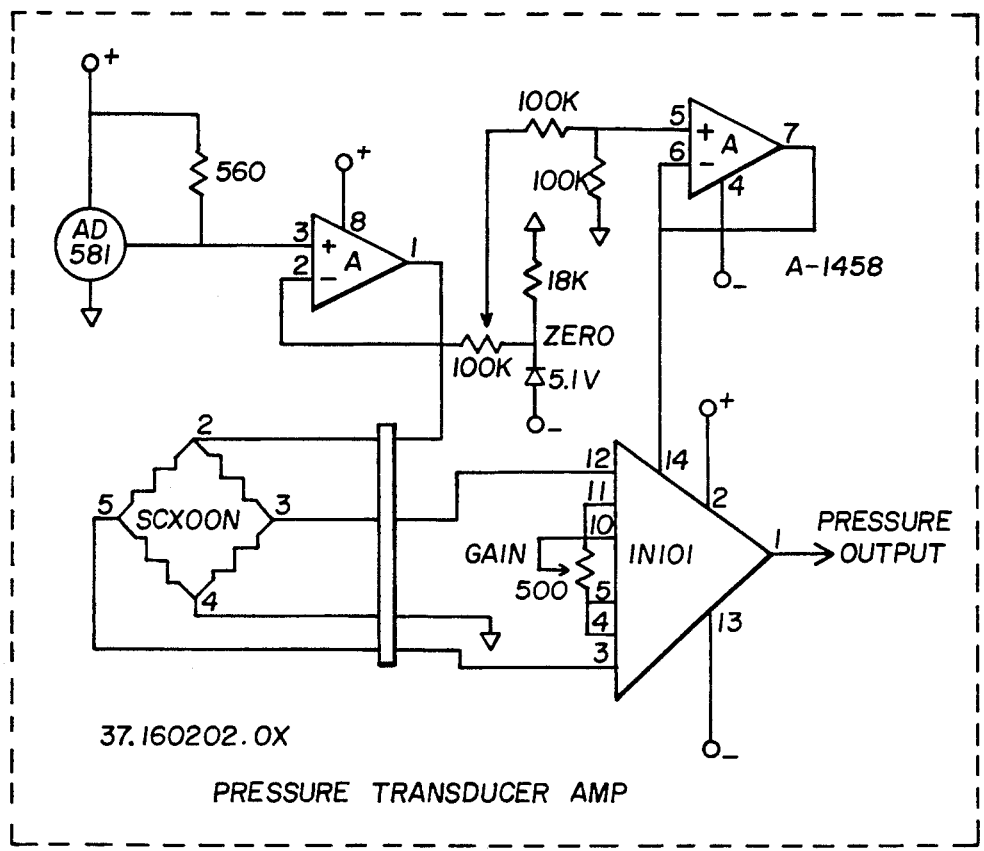
FIG. 22 shows the pressure transducer amplifier for use in the control means of FIG. 12.
Figure 23:
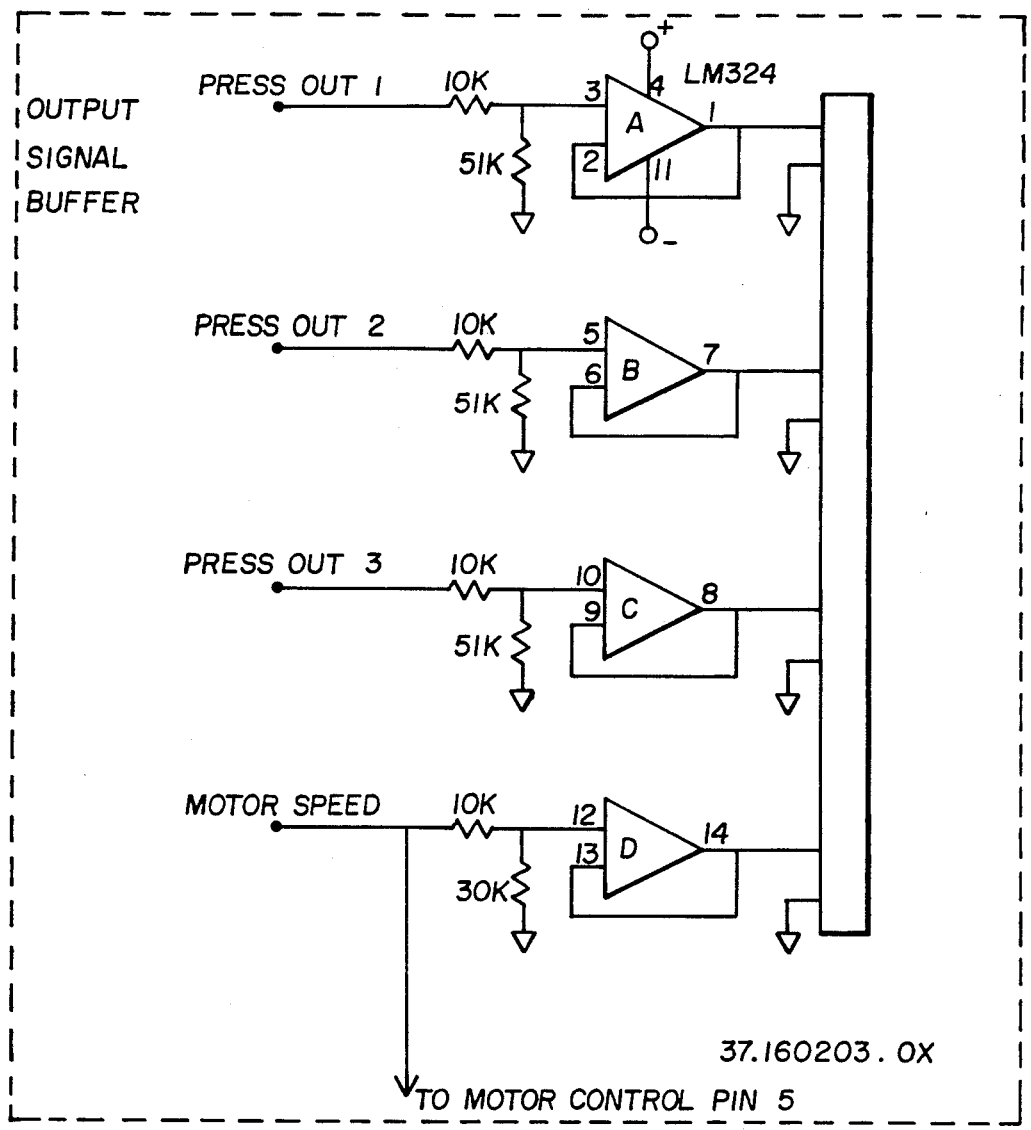
FIG. 23 shows an output signal buffer for use in the control means of FIG. 12.
Figure 24:
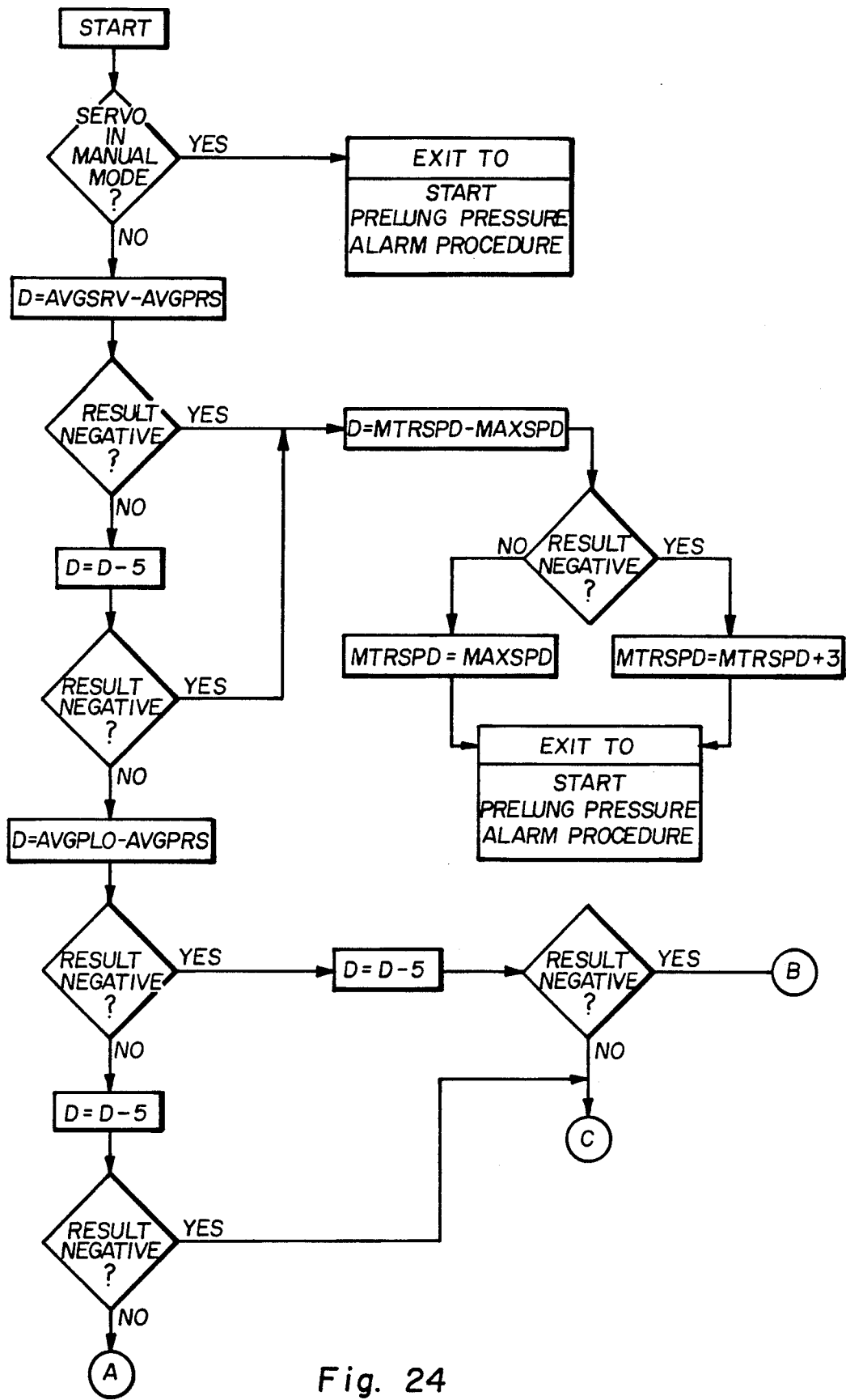
FIGS. 24 through 29 show the flow diagram of the logic within the microprocessor circuit of the control means of FIG. 12.
Figure 25:
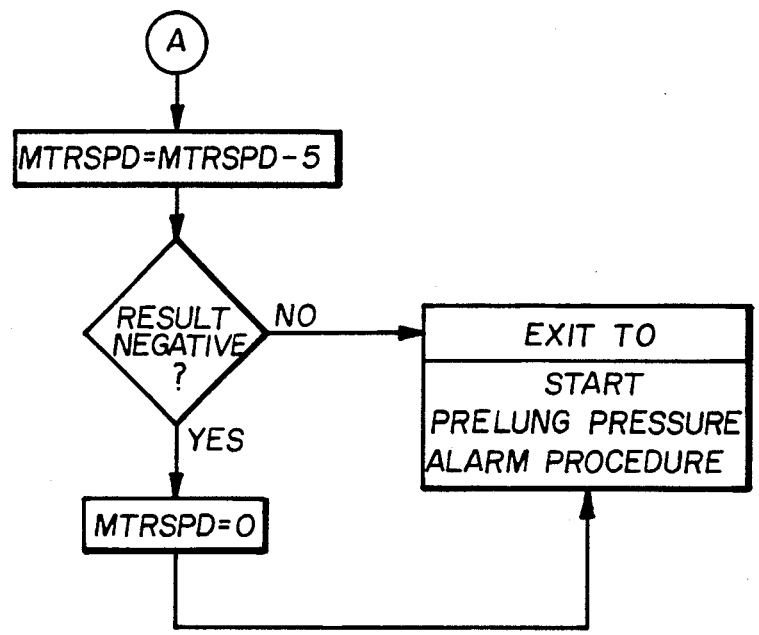
Figure 26:
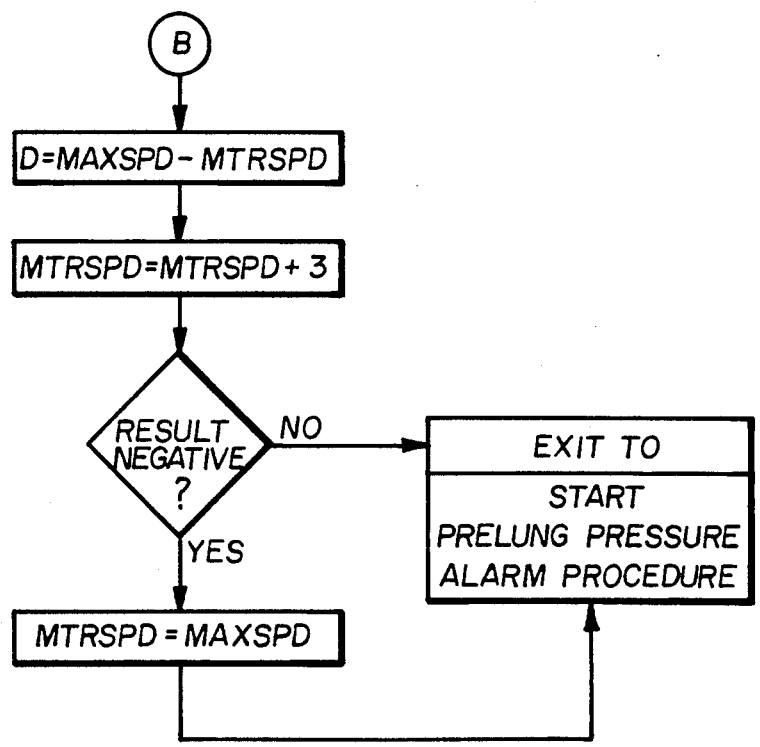
Figure 27:
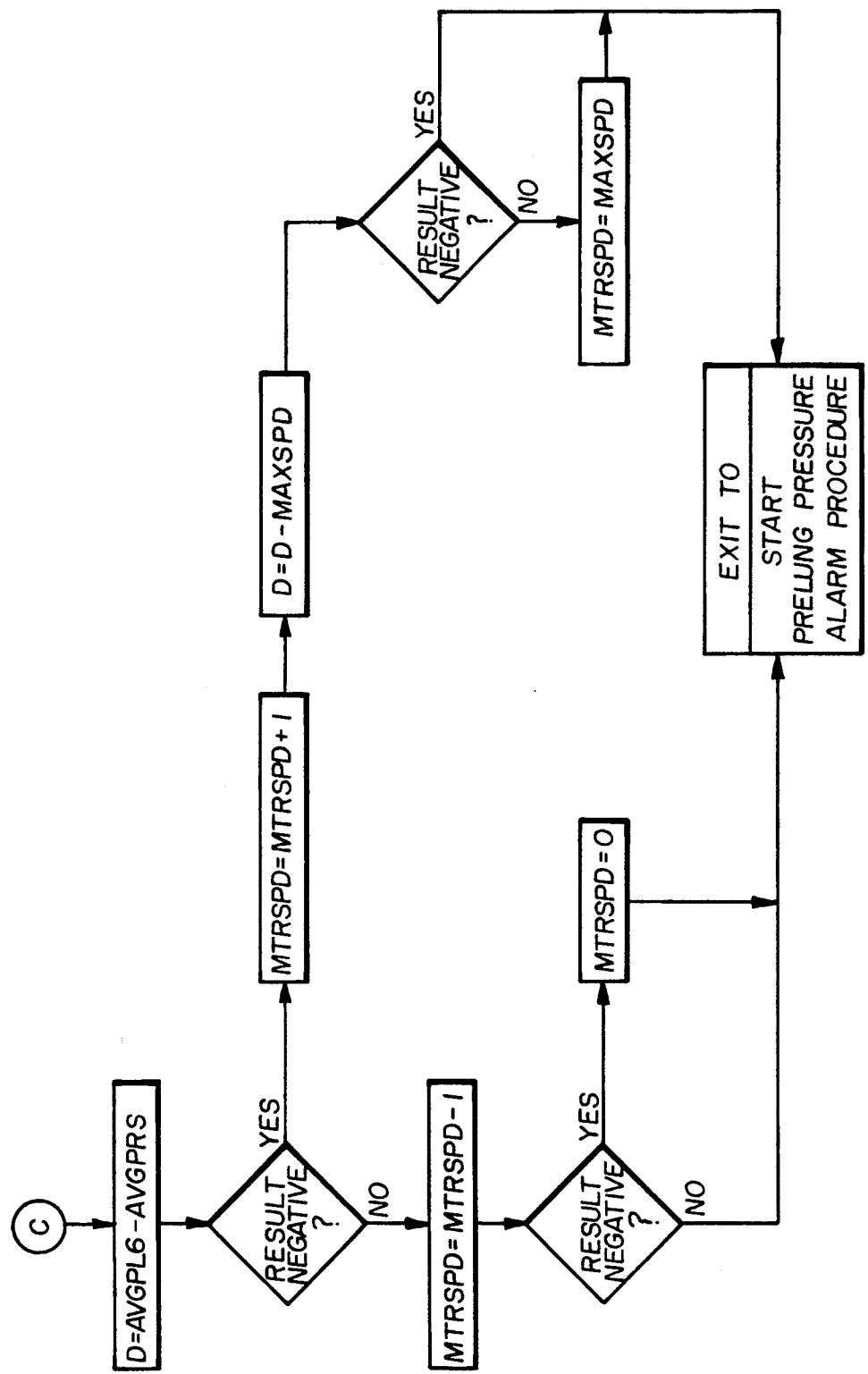
Figure 28:
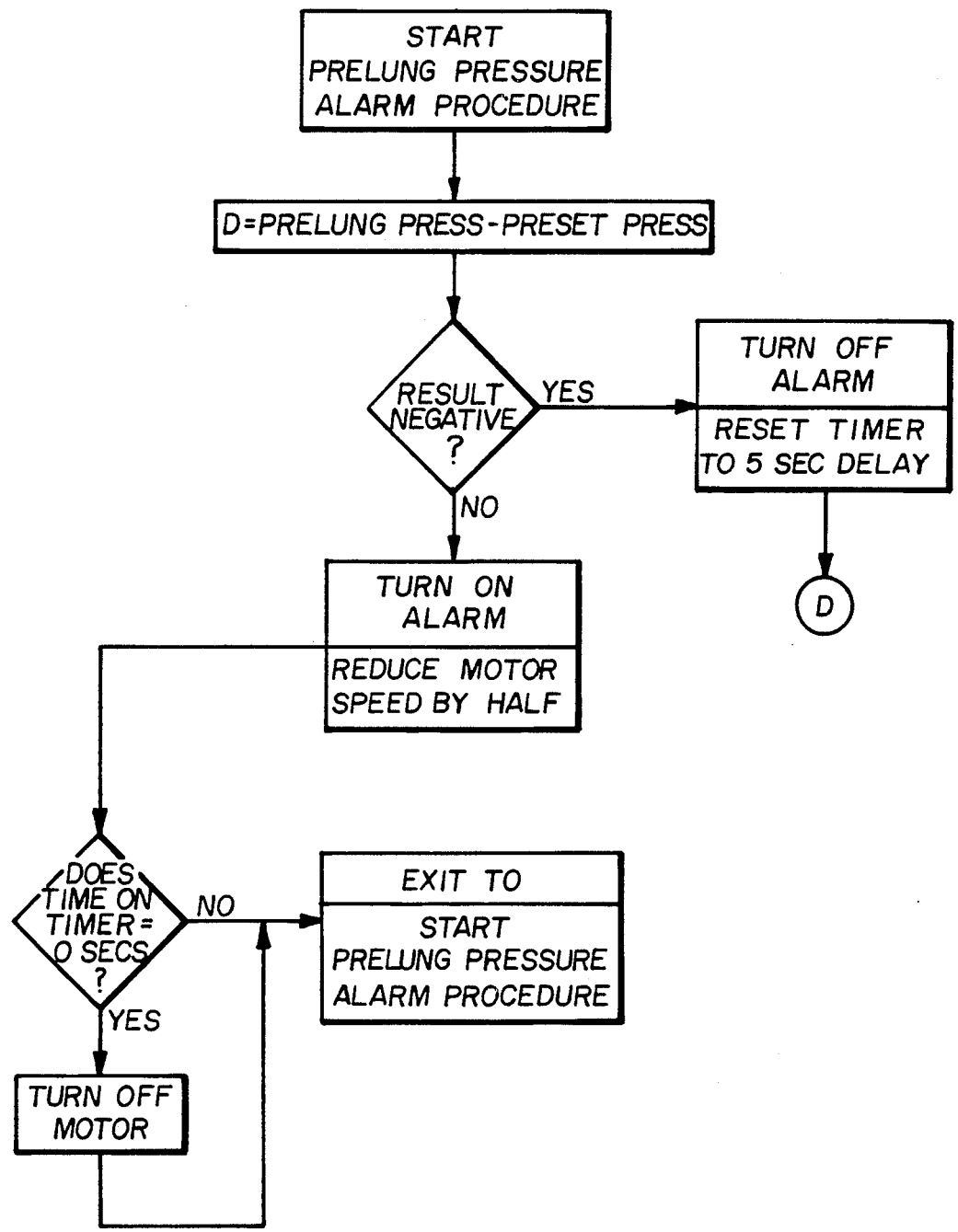
Figure 29:
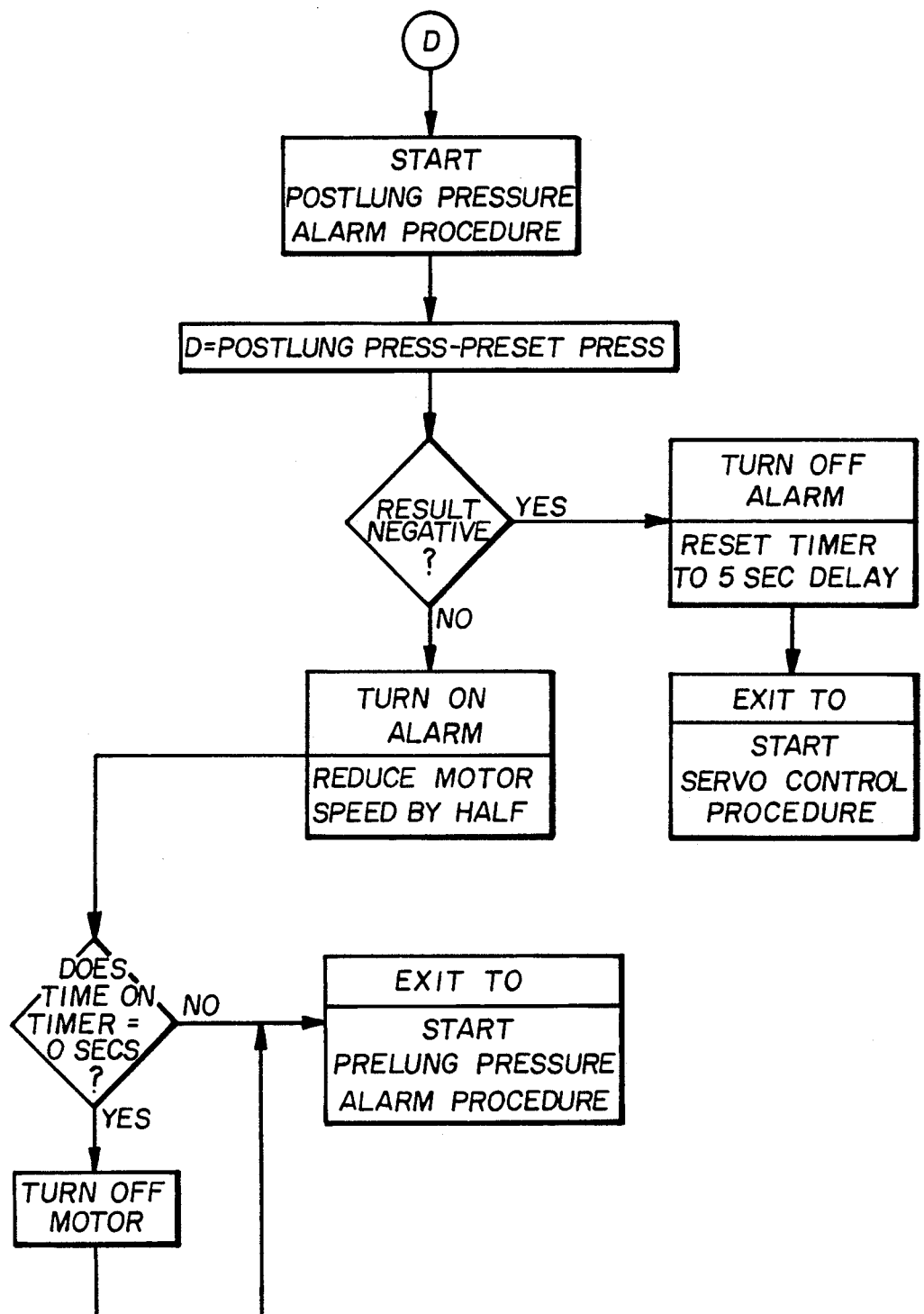

Referring now to FIG. 20 the LED array shown in the alarm section 576 of FIG. 13 is shown in greater detail. The LED's of FIG. 13 are shown with their corresponding inverter/driver. Referring now to FIG. 21, a desired circuit for use as a motor speed control is shown. The circuit is shown in the block diagram of FIG. 12 as circuit 536. Referring now to FIG. 22 a desired pressure transducer amplifier is shown for use in association with pressure sensors 30, 46, and 48 of FIG. 1. Similarly, the output signal buffer is shown in FIG. 23 as the buffer amplifier of FIG. 12.

Referring now to FIGS. 24 through 29, the architecture of the software or program in the microprocessor 625 is illustrated. Symbols include the symbol AVGPRS which means average pressure. Also shown is the symbol MTRSPD which means motor speed. The symbol MAXSPD stands for motor maximum speed. The symbol AVGPLO stands for average pressure of a sample which the zero sample.

The expression or letter "D" refers to a scratch pad holder in the microprocessor 510 in which calculations are made. The servo flow chart of FIGS. 24-29 shows automatic operation of the system of FIG. 1.

Components

The components in the system of FIG. 1, have been selected to be particularly suitable for an extracorporeal support system and more particularly an extracorporeal membrane oxygenator. For example, the first solenoid valve means is not a commercially available device, but rather is a bridge clamp or a flow blocking device illustrated and described with respect to FIG. 10A, 10B and 11. Similarly, the second solenoid means 58 and the third solenoid means 60 are also flow blocking devices illustrated with respect to FIGS. 10A, 10B and 11.

The inlet pressure sensor 30 as hereinbefore discussed is similar to that illustrated and discussed with respect to FIG. 9. The pump 28 is a pump similar to the pump 100 illustrated and described in FIGS. 2-8. The second pump means 70 is a standard syringe which is constructed to be positioned on a base 77 with motor operation device 76 as hereinbefore discussed. The controller 44 is separately manufactured and assembled as discussed with respect to FIGS. 14-29. The upstream and downstream pressure sensors 46 and 48 are preferably pressure sensors of the type illustrated and described with respect to FIG. 9.

The filter 50 in the system of FIG. 1 is preferably a 20 micron arterial filter, model K37, made by Healthdyne Cardiovascular of Marietta, Ga. The air detector is an ultrasonic scatter detector presently made by Zevex of Salt Lake City. The blood treatment device is preferably a blood oxygenator which may be a 0.6 square meters or 0.8 square meters made by Scl-Med of Minneapolis, Minn. Larger sizes are available for adults. The system blood treatment device may also be a $CO_2$ removal structure. It may also be configured for cardiopulmonary support or full bypass as well as organ preservation.

The tube 26 is preferably a Tygon® tubing of a medical grade readily available. It has been described as a single piece of tube proceeding between the connector 24 of the inlet catheter 14 and the connector 39 of the outlet catheter 36. It may also include separate tube segments, such as segment 400, 402, 404, 84, 406, 408, 410, 412, 414 and 416. Notably, segment 404 and 84 are in fact one length of tubing because it is threaded through the pump 28 as better shown by tubing 126 which is threaded through the recess 110 of pump 100 of FIG. 2.

Operations

In operation the system of FIG. 1 is operated by first positioning a system such as that illustrated in FIG. 1 near the patient 10. Blood is typically inserted into the system by operation of the pump 28 and connection to an external supply of blood particularly if the patient is a small patient such as a neonate. The system is operated to remove all air. Connection is made to the inlet catheter 14 positioned as discussed with respect to FIG. 1. The outlet catheter 36 is positioned as discussed with respect to FIG. 1. System operation may first be initiated in the manual mode, in which the operator manually operates the pump in order to initiate blood flow through the system to extract and supply blood to and from the patient at a reduced and manually controlled rate, while the patient and the patient parameters such as temperature, blood pressure and respiration are monitored to make sure the patient remains stable. Assuming the patient remains stable, set points are entered on the operation panel of FIG. 13 and automatic operation may thereafter be initiated by operation of the appropriate switches on panel 549.

When the support system of FIG. 1 is placed in the automatic mode, it may be regarded as being in the automatic servo mode. That is, the motor driving roller pump 28 such as motor 248 driving pump 100 (FIG. 2) is preferably a servomotor. Upon initiation of automatic operation, the maximum pump speed for the average pressure for the inlet pressure sensor 30 is recorded. These values thereafter can be changed only by returning to the manual operation mode to input changes by operation of the required or respective push buttons on the panel illustrated in FIG. 13.

It is believed that if the average pressure sensed by the inlet pressure sensor 30 falls below a preselected pressure then the patient's blood flow from catheter 14 is being reduced. This is interpreted by the microprocessor 510 as a indication of excessive pump speed with the risk of completely emptying the right atrium or vena cava 18 of the patient 10. As a result, the microprocessor 510 generates an output signal which causes the servomotor 248 to slow down until the slope of the pressure drop sensed by the inlet pressure sensor 30 falls to 0 or the roller pump speed/servomotor speed is 0. The microprocessor 510 attempts to operate the servomotor at the maximum speed without inducing a drop in the average pressure in the automatic operation.

In automatic operation, the upstream pressure sensor 46 supplies a pressure signal which the microprocessor interprets to generate an alarm if the pressure sensed exceeds the preselected pressure entered on panel 549. In operation it is believed that an increased pressure suggests a blockage in the blood treatment device; and such blockage may be dangerous if it becomes excessive. If an excessive pressure continues for a period in excess of 5 seconds the roller pump 28 is turned off and the alarm continues to sound until deactivated by the user or the condition is corrected by the user.

The downstream pressure sensor 48 sends its signal to the microprocessor 510 which compares it with a preset or preselected pressure. If the sensed pressure is greater than the preset pressure then an alarm condition exists and the alarm is activated on the panel section 576 of FIG. 13. The roller pump 28 is first reduced to half-speed and after 5 seconds turned off if the condition is not rectified.

Further, in operation, it may be desired first to position the system proximate the patient. As discussed, the presence of a inlet pressure sensor 30 on the upstream side 64 of the pump 28 and positioning of the distal end 16 of catheter 14 in the right atrium or vena cava 18 of the patient 10 permits selection of substantially a shorter length of tube 26. As a result the system of FIG. 1 is more easily assembled for transport of the patient in any context including emergency transportation by airplane, helicopter or the like.

In operation, the microprocessor is set to automatically flush the shunt 54 every 15 minutes to avoid coagulation and clotting in the shunt 54. That is, the blocking devices 56 and 60 close and blocking device 58 opens for about 15 seconds every 15 minutes.

It should appreciated that the illustrated embodiments are merely illustrative of the principles of the inventions which are disclosed. Specific reference to details thereof is not intended to limit the scope of the claims which themselves recite those features of the inventions which are regarded as essential thereto.

I claim:

1. A roller pump comprising:
   a housing having a top and a bottom;
   a recess formed in said housing with a surface extending inwardly from the top of said housing;
   axle means adapted to said housing in said recess to rotate relative to said housing;
   arm means secured to axle means to rotate therewith, said arm means including locking means for removably securing said arm means to said axle means and said axle means including an engagement portion for engaging said arm means, and further including a handle means having a first position extending away from said arm means and a second position in which said handle means is positioned proximate said arm means;
   roller means secured to said arm means and positioned proximate said surface for movement therealong upon rotation of said axle means;
   adjustment means interpositioned between said axle means and said arm means for moving the arm means and in turn said roller means; and
   a latch member movable between a first position in which the latch member engages the engagement portion to secure said arm means to said axle means and a second position in which the latch member is disengaged from the said engagement portion for removal of said roller means from said recess.

2. The roller pump of claim 1 wherein said surface is slanted toward said axle, wherein said roller means is a plurality of conical rollers positioned proximate said surface with the exterior surface of said rollers in substantial alignment with said surface of said recess.

3. The roller pump of claim 2 wherein said handle means is connectable to said arm means to extend away therefrom in said first position for operation by the user to rotate said arm means.

4. The roller pump of claim 3 wherein said handle means is hingedly secured to said arm means and rotatable between said first and second positions.

5. The roller pump of claim 4 further including alignment members secured to and extending away from said axle means to proximate said surface in said recess.

6. The roller pump of claim 5 wherein said housing has a front, wherein said surface is arcuate with a constant radius from said axle means, and wherein said recess includes a channel with opposite sides extending from said front.

7. A roller pump for pumping fluid through a flexible tube, said roller pump comprising:
- a housing having a top, bottom and front, said housing having a keyhole-shaped recess formed in said top extending inwardly therefrom, said recess having a throat with opposite sides opening through said front interconnecting with opposite ends of an arcuate recessed surface, said flexible tube being positionable through said front in said recess along said arcuate recessed surface;
- axle means rotatably secured to said housing and extending into said recess to be centrally positioned with respect to said arcuate surface;
- removable locking means for removably securing said pump head means to said axle means, said removable locking means including an engagement portion and a latch member positioned for operation by the user and operable between a first position in which the latch member engages the engagement portion to secure said pump head means to said from axle means and a second position in which the latch member is disengaged from said engagement portion and said pump head is removable from said axle;
- drive means connectable to said axle means to rotate said axle means relative to said housing; and
- adjustment means interpositioned between said pump head means and said axle means for moving said pump head means axially toward and away from axle means and in turn said roller means toward and away from said arcuate recessed surface.

8. The roller pump of claim 7 wherein said adjustment means includes a follower positioned to move toward and away from said axle means and screw means having a head accessible to and operable by the user with thread portions interconnecting said follower to said axle means, said screw means being operable to move said follower toward and away from said axle means.

9. The roller pump of claim 8 wherein said pump head means includes a sleeve for positioning over said follower and wherein said engagement portion includes a key way formed in said sleeve and said follower and wherein said latch is a key insertable into and removable from said key way.

10. The roller pump of claim 9 wherein said arcuate surface slants toward said axle means, and wherein said roller means includes a plurality of rollers each conically shaped with an exterior surface positioned substantially tangentially proximate said arcuate surface.

11. The roller pump of claim 10 wherein said pump head means has a central member for connection to said axle means, a top member connected to said central member, and handle means rotatably connected to said top member movable between a first position in which said handle is extended away from said pump head means and operable for rotation of said pump head means and a second position in which said handle is positioned in a stored configuration proximate said top member.

12. The roller pump of claim 11 wherein said pump head means includes a base member secured to said central member and wherein said roller means is a pair of said rollers positioned substantially diametrically opposite each other.

* * * * *

UNITED STATES PATENT AND TRADEMARK OFFICE
CERTIFICATE OF CORRECTION

PATENT NO. : 5,062,775

DATED : NOVEMBER 5, 1991

INVENTOR(S) : JEFFREY L. ORTH

It is certified that error appears in the above-identified patent and that said Letters Patent is hereby corrected as shown below:

Col. 4, line 23, please delete "form" and insert ---from---.

Col. 11, line 60, please delete "a" and insert ---an---.

Col. 12, line 43, please delete "positioned" and insert ---position---.

Col. 14, line 67, please delete "a" and insert ---an---.

Col. 15, line 54, please delete "a" and insert ---an---.

Col. 15, line 56, please delete "(LMP)" and insert ---(LPM)---.

Col. 19, line 52, please delete "a" and insert ---an---.

Col. 20, line 15, please delete "a" and insert ---an---.

Col. 20, line 28, please insert ---be--- after "should" and before "appreciate".

Col. 20, line 13, delete "5".

Col. 21, line 27, the entire paragraph as follows needs to be inserted:

---pump head means removably secured to said axle means and positioned within said recess, said pump head means including roller means positioned proximate said arcuate recessed surface for urging said flexible tube against said arcuate surface;---

UNITED STATES PATENT AND TRADEMARK OFFICE
CERTIFICATE OF CORRECTION

PATENT NO. : 5,062,775

DATED : November 5, 1991

INVENTOR(S) : Jeffrey L. Orth

It is certified that error appears in the above-identified patent and that said Letters Patent is hereby corrected as shown below:

Col. 21, line 35, please delete "from".

Signed and Sealed this

Twentieth Day of July, 1993

Attest:

MICHAEL K. KIRK

*Attesting Officer*  Acting Commissioner of Patents and Trademarks